US012478361B2

(12) United States Patent
Laub

(10) Patent No.: US 12,478,361 B2
(45) **Date of Patent: *Nov. 25, 2025**

(54) METHODS AND DEVICES FOR REMOVING A TISSUE SPECIMEN FROM A PATIENT

(71) Applicant: TDL Innovations LLC, Princeton, NJ (US)

(72) Inventor: Glenn W. Laub, Princeton, NJ (US)

(73) Assignee: TDL INNOVATIONS, LLC, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/341,444

(22) Filed: Jun. 26, 2023

(65) Prior Publication Data

US 2024/0164762 A1 May 23, 2024

Related U.S. Application Data

(63) Continuation of application No. 16/983,644, filed on Aug. 3, 2020, now Pat. No. 11,684,351, which is a (Continued)

(51) Int. Cl.

*A61B 17/00* (2006.01)
*A61B 50/00* (2016.01)
*A61B 90/00* (2016.01)

(52) U.S. Cl.

CPC ........ *A61B 17/00234* (2013.01); *A61B 50/00* (2016.02); *A61B 2017/00287* (2013.01); (Continued)

(58) Field of Classification Search

CPC ........ A61B 2217/005; A61B 2090/037; A61B 2050/0074; A61B 2050/007; (Continued)

(56) References Cited

U.S. PATENT DOCUMENTS

| | | | |
|---|---|---|---|
| 4,656,697 | A | 4/1987 | Naslund |
| 4,847,956 | A | 7/1989 | Levine |

(Continued)

FOREIGN PATENT DOCUMENTS

| | | | |
|---|---|---|---|
| WO | 9413215 | A2 | 6/1994 |
| WO | 2012046130 | A1 | 4/2012 |

OTHER PUBLICATIONS

Mitsuhiro Kamiyoshihara et al., "A useful technique for specimen extraction from the thorax: the vacuum-packing method," European Journal of Cardio-Thoracic Surgery, 0 (2012) pp. 1-3.

(Continued)

*Primary Examiner* — Jocelin C Tanner
(74) *Attorney, Agent, or Firm* — Fox Rothschild LLP

(57) ABSTRACT

A method for removing a tissue specimen from a patient includes introducing a bag at least partially into a cavity in the body of the patient, the bag comprising an open end and a port, positioning a tissue specimen to be removed from the patient into an interior of the bag by passing the tissue specimen through the open end of the bag, sealing the open end of the bag, removing gas from the interior of the bag through the port while the tissue specimen is contained in the interior of the bag, and entirely withdrawing the bag containing the tissue specimen from the cavity. The bag may include a closure device configured to hermetically seal the open end of the bag, and the port may include a one-way gas valve configured to prevent or retard gas from entering the interior of the bag through the port.

7 Claims, 28 Drawing Sheets

Related U.S. Application Data continuation of application No. 15/473,801, filed on Mar. 30, 2017, now Pat. No. 10,729,414.

(60) Provisional application No. 62/315,514, filed on Mar. 30, 2016.

(52) U.S. Cl.
CPC ............... *A61B 2017/00561* (2013.01); *A61B 2050/007* (2016.02); *A61B 2050/0074* (2016.02); *A61B 2090/037* (2016.02); *A61B 2217/005* (2013.01)

(58) Field of Classification Search
CPC ........... A61B 2017/00561; A61B 2017/00287; A61B 50/00; A61B 17/00234
USPC .......................................................... 606/114
See application file for complete search history.

(56) References Cited

U.S. PATENT DOCUMENTS 5,037,379 A * 8/1991 Clayman .......... A61B 17/00234 128/850
5,215,521 A 6/1993 Cochran et al.
5,224,930 A * 7/1993 Spaeth ................... A61B 17/34 606/128
5,332,095 A 7/1994 Wu
5,598,608 A 2/1997 Naslund
5,881,881 A 3/1999 Carrington
5,997,566 A 12/1999 Tobin
7,784,160 B2 8/2010 Dais et al.
7,874,731 B2 1/2011 Turvey et al.
8,100,874 B1 1/2012 Jordan et al.
8,172,772 B2 5/2012 Zwolinski et al.
8,202,002 B2 6/2012 McMahon et al.
8,348,827 B2 1/2013 Zwolinski
8,486,087 B2 7/2013 Fleming
8,777,961 B2 7/2014 Cabrera et al.
9,005,215 B2 4/2015 Grover et al.
11,684,351 B2 * 6/2023 Laub ................ A61B 17/00234 606/114
2003/0216611 A1 * 11/2003 Vu ......................... A61B 17/48 600/37
2003/0236486 A1 12/2003 Chang
2004/0138587 A1 7/2004 Lyons, IV
2006/0200169 A1 * 9/2006 Sniffin ............. A61B 17/00234 606/113
2007/0088370 A1 4/2007 Kahle
2008/0226203 A1 * 9/2008 Dais ................... B65D 33/2541 383/63
2008/0312496 A1 12/2008 Zwolinski
2009/0124927 A1 5/2009 Chin et al.
2009/0257688 A1 10/2009 Calvo et al.
2010/0152746 A1 6/2010 Ceniccola
2010/0219091 A1 9/2010 Turner
2011/0184431 A1 * 7/2011 Parihar .................. A61B 17/00 606/114
2011/0190779 A1 8/2011 Gell et al.
2011/0190781 A1 * 8/2011 Collier ............. A61B 17/00234 606/114
2011/0270265 A1 11/2011 Fleming
2011/0299799 A1 12/2011 Towe
2012/0083795 A1 4/2012 Fleming et al.
2012/0232423 A1 9/2012 Menn et al.
2012/0277758 A1 11/2012 Davis et al.
2013/0184536 A1 7/2013 Shibley et al.
2013/0218170 A1 8/2013 Uznanski et al.
2013/0325025 A1 12/2013 Hathaway et al.
2014/0052018 A1 2/2014 Hawkins
2015/0305772 A1 10/2015 McCauley
2016/0199050 A1 7/2016 Radl et al.
2017/0049427 A1 * 2/2017 Do ..................... A61B 17/3431

OTHER PUBLICATIONS

Genicon GENIStrong Specimen Retrieval Bag, 2015 Brochure (2 pages).

Andreas Stavroulis et al., "Methods for specimen removal from the peritoneal cavity after laparoscopic excision," The Obstetrician & Gynaecologist, 15 (2013), pp. 26-30.

International Search Report and Written Opinion of the International Searching Authority, dated Jun. 9, 2017, for International Application No. PCT/US2017/024887.

* cited by examiner

METHODS AND DEVICES FOR REMOVING A TISSUE SPECIMEN FROM A PATIENT

CROSS-REFERENCE TO RELATED APPLICATIONS

This application claims the benefit of U.S. Provisional Patent Application No. 62/315,514, filed Mar. 30, 2016, which is incorporated herein by reference in its entirety.

FIELD OF THE INVENTION

The present invention, according to some embodiments, relates to methods and devices for removing a tissue specimen from a patient. More particularly, some embodiments of the present invention relate to methods for removing a tissue specimen using a bag that can be evacuated of gas to compress the tissue specimen. In further embodiments, the present invention relates to a bag that can be used for tissue specimen removal in accordance with the methods described herein. In other embodiments, the present invention relates to a clip which may be used to create a hermetic seal around a suctioning device.

BACKGROUND OF THE INVENTION

Certain surgical procedures, for example, lobectomy, nephrectomy, cystectomy, etc., involve the removal of a tissue specimen from the interior of a patient's body. The tissue specimen to be removed may include, for example, an organ or portion thereof that is damaged, diseased, or tumorous. The affected tissue may be surgically cut and removed from the body using either conventional or minimally invasive surgery.

Conventional surgery (i.e., open surgery) requires large areas of the patient's body to be cut open in order to provide the surgeon with access to the affected tissue. In contrast, minimally invasive surgery (e.g., laparoscopy, endoscopy) utilizes narrow, elongated instruments to access the affected tissue through relatively small incisions. It is often preferable to use minimally invasive surgical techniques in order to reduce trauma and recovery time for the patient. Some techniques involve, for example, inserting a specimen bag into the patient's body through an access incision, placing the bag around the tissue to be removed, and withdrawing the bag containing the tissue from the patient's body. The specimen bag may include a drawstring closure and may further be connected to specialized equipment for manipulating the bag. Various surgical techniques and devices have been described, for example, in U.S. Pat. Nos. 5,037,379, 5,215,521, 8,172,772, 8,486,087, 8,777,961, 9,005,215, U.S. Patent Application Publication No. US 2004/0138587 A1, U.S. Patent Application Publication No. 2009/0124927 A1, U.S. Patent Application Publication No. US 2012/0232423 A1, U.S. Patent Application Publication No. US 2013/0184536 A1, U.S. Patent Application Publication No. 2013/0325025 A1, each of which is incorporated by reference herein in its entirety.

A difficulty that may be encountered during certain minimally invasive surgical procedures occurs when the tissue specimen to be removed is significantly larger than the access incision. Under these circumstances the access incision may be enlarged or a new incision may be required in order to allow passage and retrieval of the tissue specimen, however, such steps would increase the trauma to the patient. Another method involves cutting or morcellating the tissue specimen into smaller pieces in the specimen bag until the fragmented tissue can be removed through the access incision. However, this method can result in further complications, such as rupturing of the specimen bag by the cutting or morcellating tool. Moreover, when the tissue being cut or morcellated is cancerous, there may also be an increased risk of spreading cancer cells during such procedures.

A further method for tissue removal is described in Mitsuhiro Kamiyoshihara et al., "A useful technique for specimen extraction from the thorax: the vacuum-packing method," European Journal of Cardio-Thoracic Surgery, 0 (2012) pp. 1-3, which is also incorporated herein by reference in its entirety. According to this method a sucker is inserted into the opening of the specimen bag to suck out liquid and air from the bag in order to collapse the bag containing the tissue specimen, the collapsed bag being withdrawn from the patient as the bag is being suctioned. Since the sucker extends through the bag opening, a drawback of the method described by Kamiyoshihara et al. is that it may be difficult to create and sustain a sufficient seal to allow for proper vacuuming to occur. Having to add binding material around the bag and sucker to create a proper seal adds further to the complication of the procedure. Moreover, there is a risk that insertion of the sucker or other tools into the bag could puncture or tear the bag.

SUMMARY OF THE INVENTION

The present invention, according to some embodiments, provides methods and bags for removing a tissue specimen from the body of a patient that can avoid some of the difficulties and drawbacks described above. As used herein, a patient may refer to a human patient, or in other embodiments, patient may also refer to non-human animals, for example, veterinary patients. In some embodiments, the tissue specimen is an internal organ or a portion thereof, for example, a portion of the patient's lung. In some embodiments, the tissue specimen includes a tumor, cyst, cancer, or other diseased tissue. The tissue specimen to be removed may be located in a cavity in the body of the patient, for example, the chest cavity or abdomen.

While embodiments described herein are discussed in the particular context of removing a tissue specimen from a patient, it should be appreciated that the present invention is not necessarily limited to this use. Certain methods and bags of the present invention may be more generally adapted for retrieving other objects, including non-biological objects. In some embodiments, the present invention includes a general method for retrieving an object from a first side of a barrier through an opening in the barrier. In some embodiments, the object to be retrieved has a dimension which is larger than a broadest dimension of the opening. In some embodiments, the object is a soft, flexible and/or compressible object. In some embodiments, a method according to the present invention includes introducing a bag at least partially through the opening from a second side of the barrier to the first side of the barrier, the bag comprising an open end and a port. In some embodiments, at least the open end of the bag is introduced through the opening to the first side of the barrier. In some embodiments, the method further includes positioning the object to be retrieved into an interior of the bag by passing the object through the open end of the bag, sealing the open end of the bag, removing gas from the interior of the bag through the port while the object is contained in the interior of the bag, and entirely withdrawing the bag containing the object from the first side of the barrier to the second side of the barrier through the opening. In some embodiments, the open end of the bag includes a closure device configured to hermetically seal the open end of the bag. In some embodiments, the closure device includes interlocking components configured to form a hermetic seal, for example, a zipper closure. In further embodiments, the port includes a one-way gas valve configured to prevent or at least retard gas from entering the interior of the bag through the port. In some embodiments, the port is configured to be coupled with a suctioning device which is configured to remove the gas from the interior of the bag through the port. In some specific embodiments, the object may be a tissue specimen of a patient (e.g., lung tissue), the barrier may be a body wall of the patient (e.g., chest cavity wall), and the opening may be an incision made in the body wall.

In further embodiments of the present invention, a method for removing a tissue specimen from a patient includes introducing a bag at least partially into a cavity in the body of the patient, the bag having an open end and a port having a valve, positioning the tissue specimen to be removed from the patient into an interior of the bag by passing the tissue specimen through the open end of the bag, sealing the open end of the bag, removing gas from the interior of the bag through the port while the tissue specimen is contained in the interior of the bag, and withdrawing the bag containing the tissue specimen from the cavity. In some embodiments, inserting the bag at least partially through a first incision in a body wall defining the cavity. In some embodiments, introducing the bag at least partially into the cavity includes inserting the bag into the cavity through a sleeve. In some embodiments, the bag may be inserted into the cavity in a folded or rolled state. In other embodiments, the bag may be inserted through the first incision into the cavity by hand without the use of any tools. In some embodiments, at least the open end of the bag is positioned within the cavity when the tissue specimen is inserted through the open end of the bag.

In some embodiments, the method further includes withdrawing the open end of the bag from the cavity prior to sealing the open end of the bag. In some embodiments, sealing the open end of the bag includes hermetically sealing the open end of the bag. In some embodiments, the open end of the bag includes a closure device configured to hermetically seal the open end of the bag. In some embodiments, the closure device is configured to be closed by hand without the use of any tools or additional binding material. In some embodiments, the closure device includes interlocking components configured to form a hermetic seal, for example, a zipper closure. In yet other embodiments, the open end of the bag may be heat sealed or sealed with adhesive.

In some embodiments, the port of the bag is positioned outside of the cavity when the gas is removed from the interior of the bag through the port. As used herein, a gas refers to a substance in a gas phase, including vapors. In some embodiments, the port includes a one-way gas valve configured to prevent or at least retard gas from entering the interior of the bag through the port. In some embodiments, the port can be coupled with a suctioning device which is configured to remove the gas from the interior of the bag through the port. The suctioning device may be, for example, a hand-held vacuum gun or other vacuum source. In certain embodiments, no portion of the suctioning device is inserted into the interior of the bag. In some embodiment, removing gas from the interior of the bag reduces the volume of the interior of the bag. In some embodiments, the suctioning device or vacuum source is uncoupled from the port of the bag prior to entirely withdrawing the bag containing the tissue specimen from the cavity. In some embodiments, entirely withdrawing the bag containing the tissue specimen from the cavity includes withdrawing the bag from the cavity through the first incision. In some embodiments, withdrawing the bag from the cavity through the first incision does not require enlarging the first incision.

In further embodiments, the bag may include a spring element configured to open the open end of the bag. In some such embodiments, the spring element is a loop or portion thereof made from an elastic material which extends at least partially around the open end of the bag. The spring element may be made from, for example, an elastic metal, alloy, plastic, polymer, or composite material. In some embodiments, the spring element is compressed prior to introducing the bag at least partially into the cavity in the body of the patient. The bag may also be coiled prior to introducing the bag at least partially into the cavity in the body of the patient. After the bag is introduced into the cavity, the spring element may be allowed to spring open in order to open the open end of the bag prior to positioning the tissue specimen into the interior of the bag. In further embodiments, the spring element may be separated from the bag prior to sealing the open end of the bag. In some embodiments, the spring element is separated from the bag after positioning the tissue specimen to be removed from the patient into the interior of the bag. In some such embodiments, the bag includes a tear line positioned between the spring element and the closure device, the tear line being configured to allow the spring element to be torn off of the bag. The tear line may be, for example, a line of perforations on the wall of the bag. After the spring element is removed from the bag, the closure device may be sealed and the gas evacuated from the interior of the bag through the port to compress the bag and the tissue specimen contained therein.

The present invention, according to additional embodiments, provides a method for removing an object from a cavity which includes introducing a bag at least partially into a cavity, the bag comprising an open end, positioning an object to be removed into an interior of the bag by passing the object through the open end of the bag, inserting a suctioning device into the interior of the bag through the open end of the bag, positioning a clip in an open configuration around the bag and the suctioning device, transitioning the clip to a closed configuration to hermetically seal the bag around the suctioning device, removing gas from the interior of the bag with the suctioning device while the object is contained in the interior of the bag, and entirely withdrawing the bag containing the object from the cavity. In some such embodiments, the bag does not need to include a closure device for hermetically sealing the bag. Moreover, the bag does not need to include a port for coupling with a suction device. In some embodiments, the object is a tissue specimen (e.g., lung tissue) of a patient, and the cavity is a body cavity of the patient. In some embodiments, the clip includes a first leg and a second leg, and transitioning the clip to the closed configuration includes moving the first leg and the second leg towards each other. In certain embodiments, the first leg and the second leg are connected by a hinge portion (e.g., a living hinge) configured to allow the first leg and the second leg to pivot toward each other. In some embodiments, the clip further includes a closure (e.g., a latch) for securing the first leg and the second leg together in the closed configuration. In some embodiments, the first leg and the second leg are shaped to define an opening between the first leg and the second leg in the closed configuration, the opening being sized and configured to receive the suctioning device. In some embodiments, at least one of the first leg and the second leg includes a concavely curved internal surface which at least partially defines the opening. In some such embodiments, positioning the clip in an open configuration around the bag and the suctioning device comprises positioning the concavely curved internal surface around a portion of the suctioning device. The suctioning device may include a catheter and, in some embodiments a cuff may be placed around at least a portion of the catheter. In these embodiments, the concavely curved internal surface of the first or second leg of the clip may be positioned around the cuff.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention can be embodied in different forms and thus should not be construed as being limited to the embodiments set forth herein.

DETAILED DESCRIPTION

The present subject matter will now be described more fully hereinafter with reference to the accompanying Figures, in which representative embodiments are shown. The present subject matter can, however, be embodied in different forms and should not be construed as limited to the embodiments set forth herein. Rather, these embodiments are provided to describe and enable one of skill in the art. All publications, patent applications, patents, and other references mentioned herein are incorporated by reference in their entirety.

Figure 1:
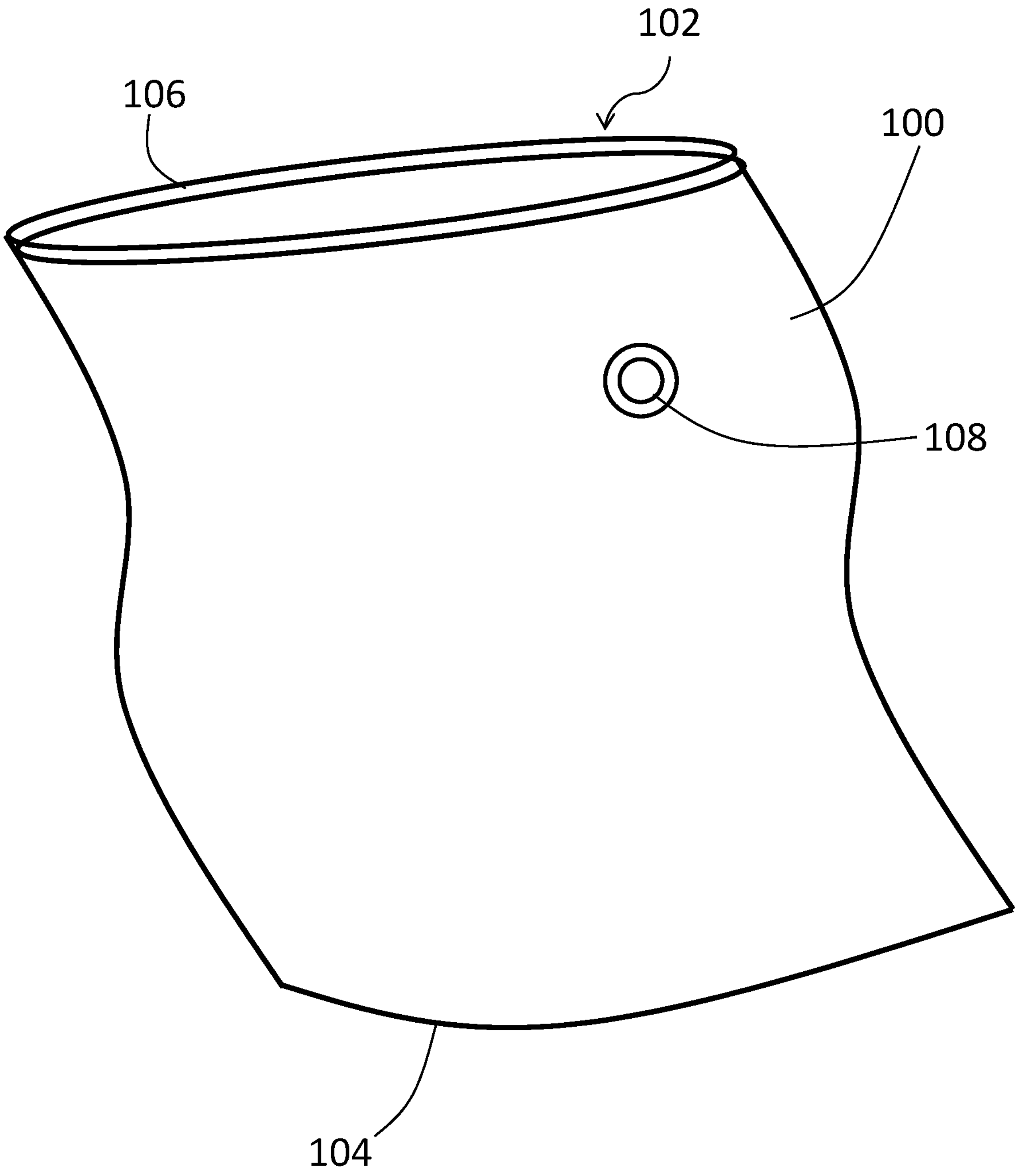
FIG. 1 shows a tissue specimen bag according to an embodiment of the present invention.

Referring to the drawings in detail, wherein like reference numerals indicate like elements throughout, there is shown in FIGS. 1-9, a bag configured for tissue specimen removal generally designated 100, in accordance with an exemplary embodiment of the present invention. As illustrated in FIG. 1, bag 100 includes an open end 102 and a closed end 104 opposite open end 102. The walls of bag 100, which extend between open end 102 and closed end 104, define an interior space and may be constructed from thin, flexible plastic film, for example, polyethylene, nylon, vinyl, ripstop, etc. Bag 100 may have any suitable shape when fully extended, for example, cylindrical, conical, rectangular, etc. In some embodiments, bag 100 may be tapered at closed end 104. Other bag shapes, for example, as described in the references incorporated herein may also be utilized according to further embodiments of the present invention. The walls of bag 100 are preferably waterproof and may be completely sealed at their edges except for open end 102 according to some embodiments. Open end 102 provides access to the interior space of bag 100 and, in some embodiments, includes a closure device 106 that is configured to close and seal open end 102. Closure device 106 may be integral to bag 100. Closure device 106, in some embodiments, may include interlocking components configured to form a hermetic seal. For example, in some embodiments, closure device 106 is a zipper closure that is configured to produce an airtight seal. In some embodiments, bag 100 does not include or require a drawstring closure. In further embodiments, the walls of bag 100 are provided with a port 108, which may be configured to allow gas to exit from the interior of bag 100. In some embodiments, port 108 is positioned proximate open end 102. In some embodiments, port 108 is positioned on bag 100 between closure device 106 and closed end 104. In some embodiments, only a single port is provided on bag 100. In other embodiments, bag 100 may include a plurality of ports. Port 108, in some embodiments, is further provided with a valve, for example, a one-way gas valve that is configured to prevent or retard gas from re-entering into the interior of bag 100 through port 108.

Non-limiting example configurations for closure devices, valves, and materials that may be adapted for use in bag 100 according to some embodiments of the present invention are described in U.S. Pat. Nos. 5,332,095, 5,881,881, 7,784,160, 7,874,731, 8,202,002, and U.S. Patent Application Publication No. US 2009/0257688 A1, all of which are incorporated herein by reference in their entireties. Unlike the bags described in these references, however, bag 100 according to embodiments of the present invention may be particularly configured for surgical use. In some embodiments, for example, bag 100 is sterilized such that bag 100 is free of bacteria, fungi, or other viable microorganisms. In some embodiments, bag 100 is sterilized with radiation, heat, steam, chemical treatments, or a combination thereof. In some embodiments, bag 100 is provided with an anti-microbial substance or coating. In yet further embodiments, bag 100 may be provided with a radiopaque element to allow for visualization using radiographic or fluoroscopic imaging techniques. For example, open end 102 or another portion of bag 100 may be provided with a radiopaque marker or thread such that the surgeon can determine the presence, location, and/or orientation of bag 100 inside the patient's body through radiographic or fluoroscopic imaging.

Figure 2:
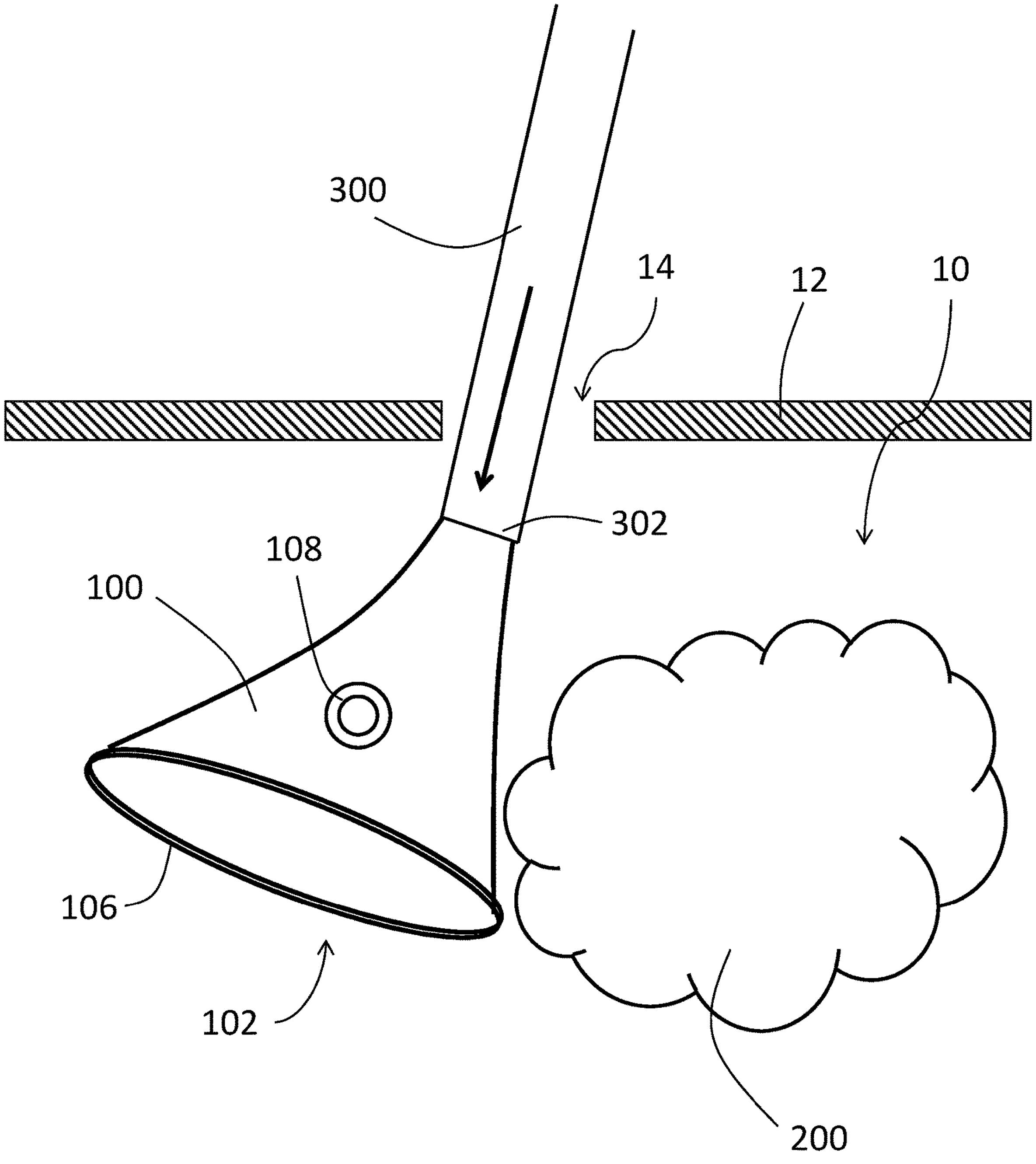
FIG. 2 shows the tissue specimen bag of FIG. 1 being introduced through an incision into a cavity in the body of a patient using a sleeve according to one embodiment of the present invention.

In some embodiments, bag 100 is sufficiently flexible to be tightly folded or rolled such that bag 100 can be fit through a small incision and into a cavity in the body of a patient. In some embodiments, bag 100 may be folded or rolled inside a sleeve that is configured to introduce bag 100 through the incision and into the cavity. FIG. 2 shows bag 100 being introduced at least partially into a cavity 10 in the body of a patient through an incision 14 in a body wall 12 according to one embodiment of the present invention. Tissue specimen 200 to be removed from the patient is located within cavity 10. For example, cavity 10 may be a thoracic cavity of the patient, body wall 12 may represent the chest wall, and tissue specimen 200 may represent a portion of lung tissue which has been cut from the patient. As shown in this embodiment, bag 100 may be introduced through incision 14 and into cavity 10 using a sterile sleeve 300. Sleeve 300, according to some embodiments, may be a tube, trocar, or endoscopic instrument having an end 302 that is sized and configured to pass through incision 14 and into cavity 10. In some embodiments, bag 100 is packaged within sleeve 300 until use. End 302 of sleeve 300 may include a radiopaque marker to allow for radiographic or fluoroscopic imaging. Once end 302 of sleeve 300 is sufficiently positioned within cavity 10, bag 100 may be pushed or pulled out of sleeve 300 through end 302 and into cavity 10. In other embodiments, bag 100 may be inserted through incision 14 without the use of a sleeve. For example, in some embodiments, a surgeon may fold or roll bag 100 into a size compact enough to be inserted through incision 14 by hand or by using a tool, such as laparoscopic forceps. In some embodiments, bag 100 is not affixed to any tools when bag 100 is introduced into cavity 10.

Figure 3:
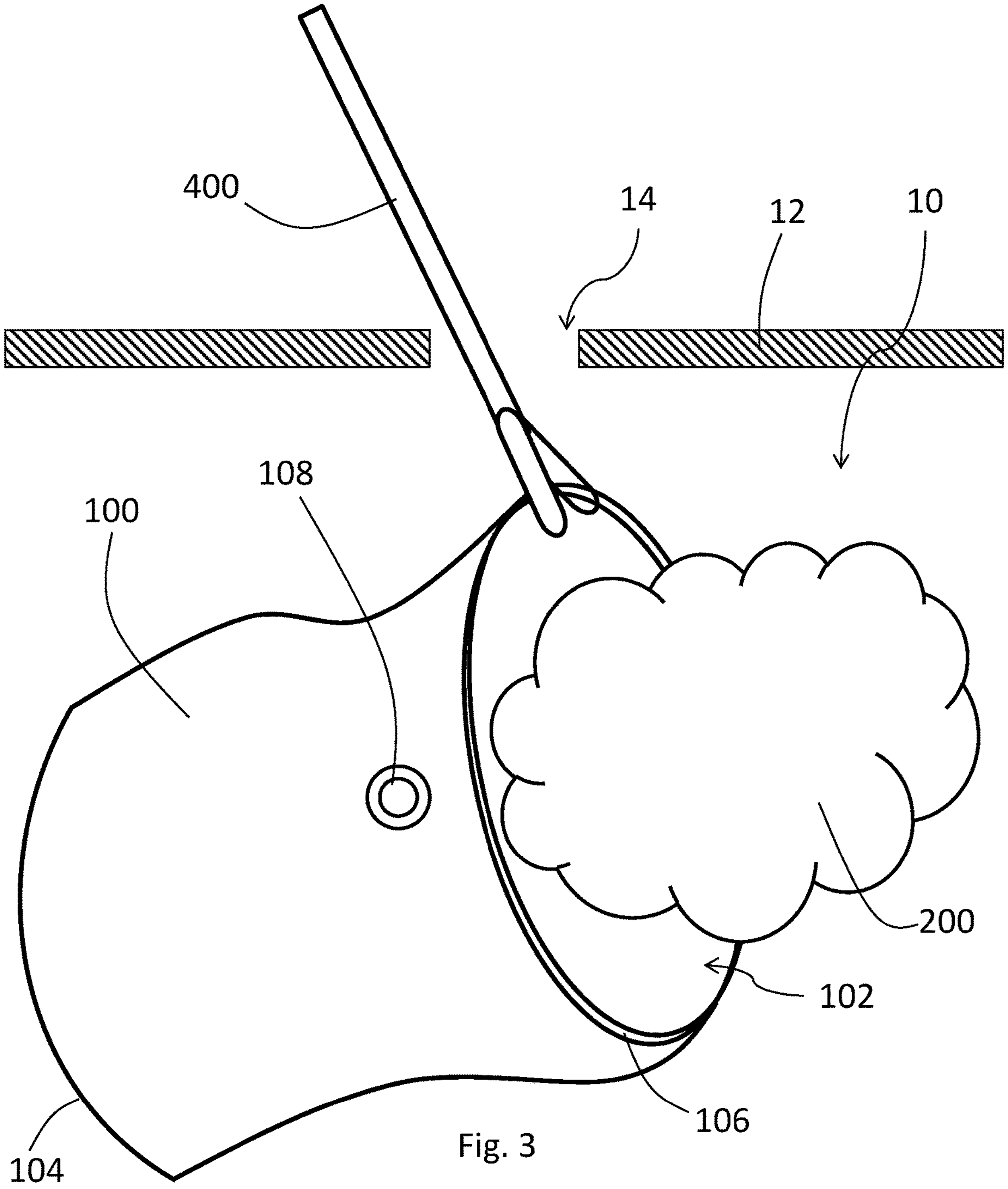
FIG. 3 shows a tissue specimen passing through the open end of the specimen bag of FIG. 2 according to one embodiment of the present invention.
Figure 4:
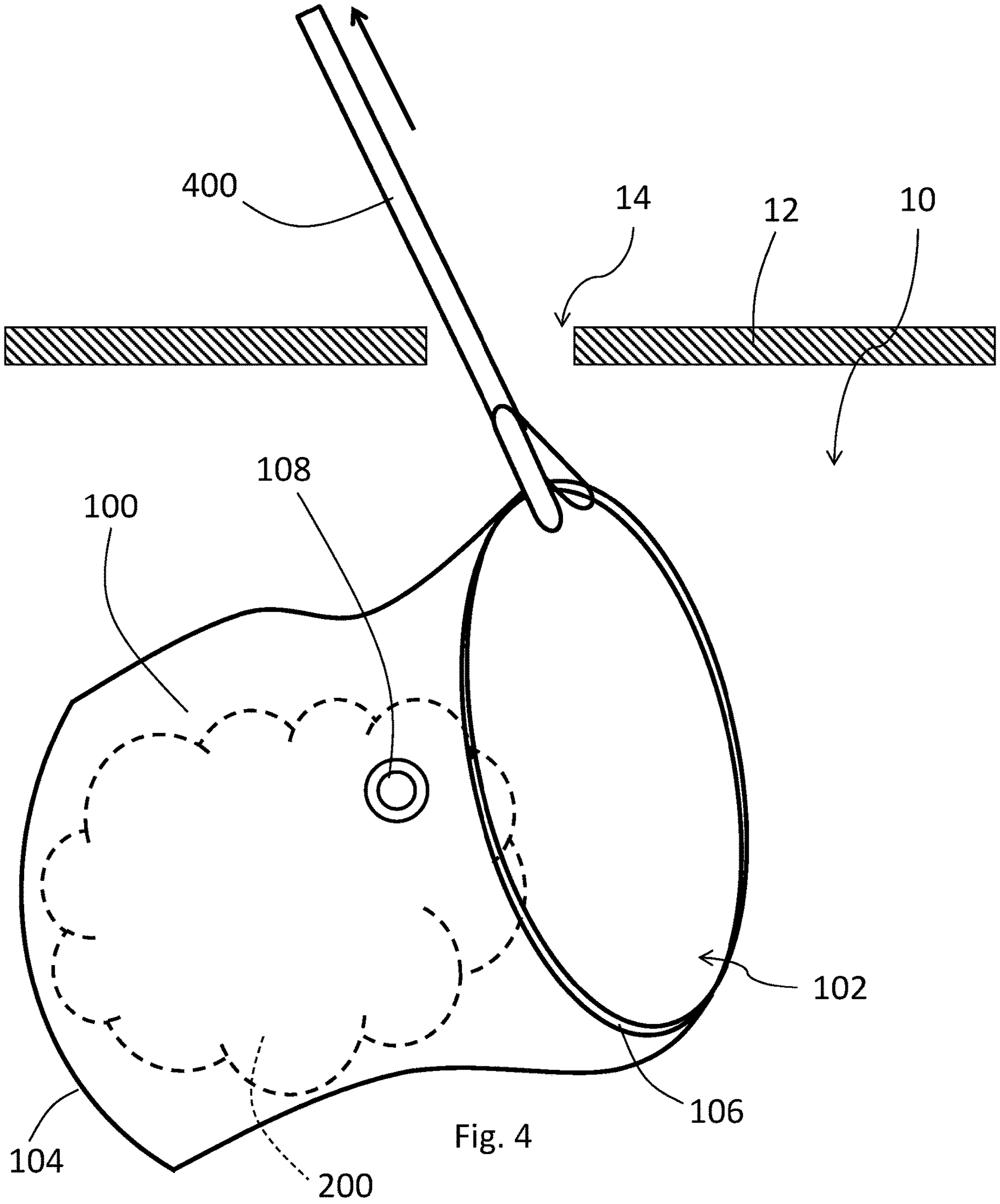
FIG. 4 shows the tissue specimen of FIG. 3 fully positioned within the interior of the tissue specimen bag according to one embodiment of the present invention.

Referring now to FIGS. 3 and 4, tissue specimen 200 may be passed through open end 102 and positioned into the interior of bag 100 while bag 100 is positioned within cavity 10. In some embodiments, one or more removable tools 400, for example laparoscopic forceps, may be optionally used to assist with positioning tissue specimen 200 within the interior of bag 100. For example, one or more tools 400 may be used to spread open end 102 wider and/or push tissue specimen 200 through open end 102 into the interior of bag 100. Such one or more tools 400 are preferably separable from bag 100 and not affixed to bag 100. Once tissue specimen 200 is positioned within the interior of bag 100, open end 102 may be sealed. In some embodiments, open end 102 may be sealed within cavity 10. In other embodiments, it may be preferable to withdraw open end 102 from cavity 10 prior to sealing open end 102. Withdrawing open end 102 from cavity 10 may facilitate sealing of open end 102 according some of these embodiments since the surgeon may have better access to open end 102. In some embodiments, the one or more tools 400 (e.g., forceps) are used to pull open end 102 of bag 100 out of cavity 10 through incision 14 in body wall 12. In other embodiments, open end 102 may be pulled out of cavity 10 by hand, without the use of any additional tools.

Figure 5:
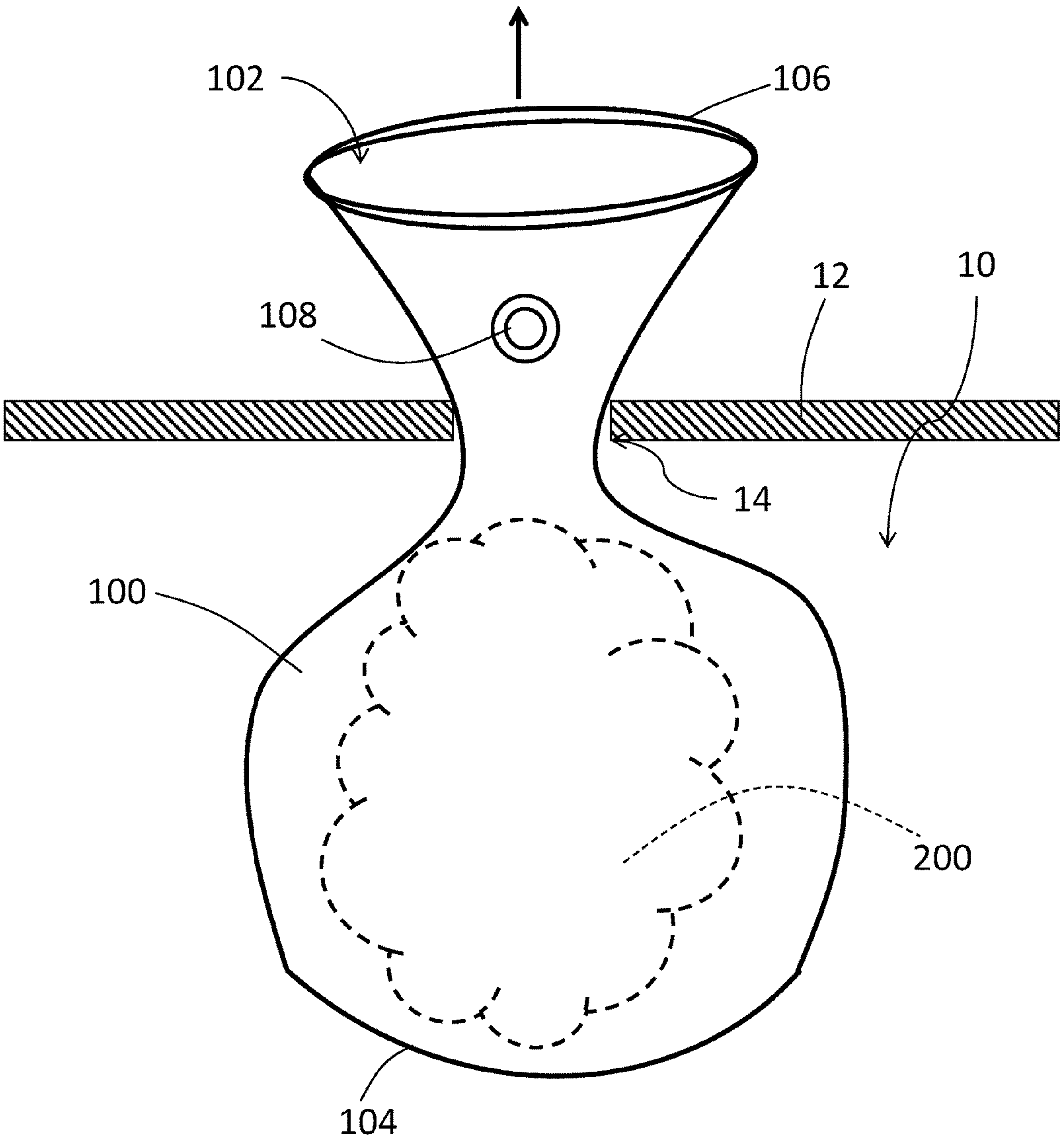
FIG. 5 shows the open end and port of the tissue specimen bag of FIG. 4 withdrawn from the cavity according to one embodiment of the present invention.

FIG. 5 shows bag 100 at least partially withdrawn from cavity 10. In particular, open end 102 has been withdrawn from cavity 10 through incision 14 while a portion of bag 100 containing tissue specimen 200, which may be too large to fit through incision 14, remains within cavity 10. In some embodiments, port 108 may also be withdrawn from cavity 10 such that both open end 102 and port 108 are positioned outside of cavity 10. In some embodiments, a cutting tool or morcellator (not shown) may optionally be introduced into the interior of bag 100 through open end 102 in order to cut tissue specimen 200 into smaller fragments. However, as discussed above, such steps may not be preferred and may not be necessary according to embodiments of the present invention. In some embodiments, no cutting or morcellation of tissue specimen 200 occurs while tissue specimen 200 is in the interior of bag 100.

Figure 6:
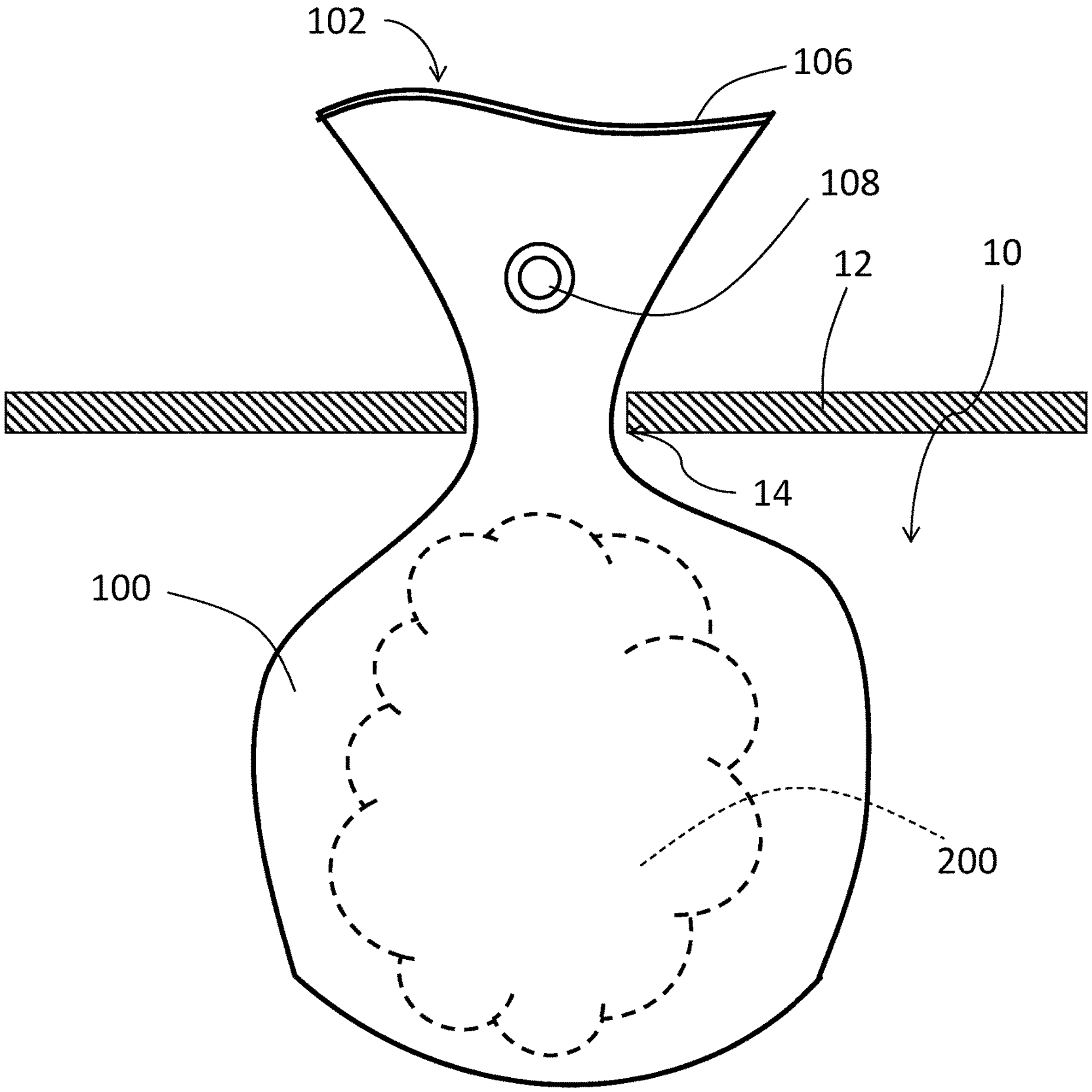
FIG. 6 shows the tissue specimen bag of FIG. 5 after sealing the open end of the bag according to one embodiment of the present invention.

After open end 102 of bag 100 is positioned outside of cavity 10, open end 102 may be sealed using closure device 106 as shown in FIG. 6. As discussed above, closure device 106 is particularly configured to hermetically seal open end 102. Unlike the drawstring closure used previously in the art which may not be able to achieve a hermetic seal, in some embodiments, closure device 106 includes interlocking components, for example, a zipper closure. Closure device 106 may be configured to be closed by hand to form a hermetic seal without the use of additional tools or binders according to some embodiments. In some embodiments, closure device 106 is capable of being unsealed and resealed such that open end 102 may be reopened and resealed if needed. In other embodiments, open end 102 may be permanently sealed such that bag 100 must be cut or torn to open bag 100. In some such embodiments, for example, open end 102 may be heat sealed. In yet other embodiments, open end 102 may be sealed with adhesive (e.g., cyanoacrylate glue).

Figure 7:
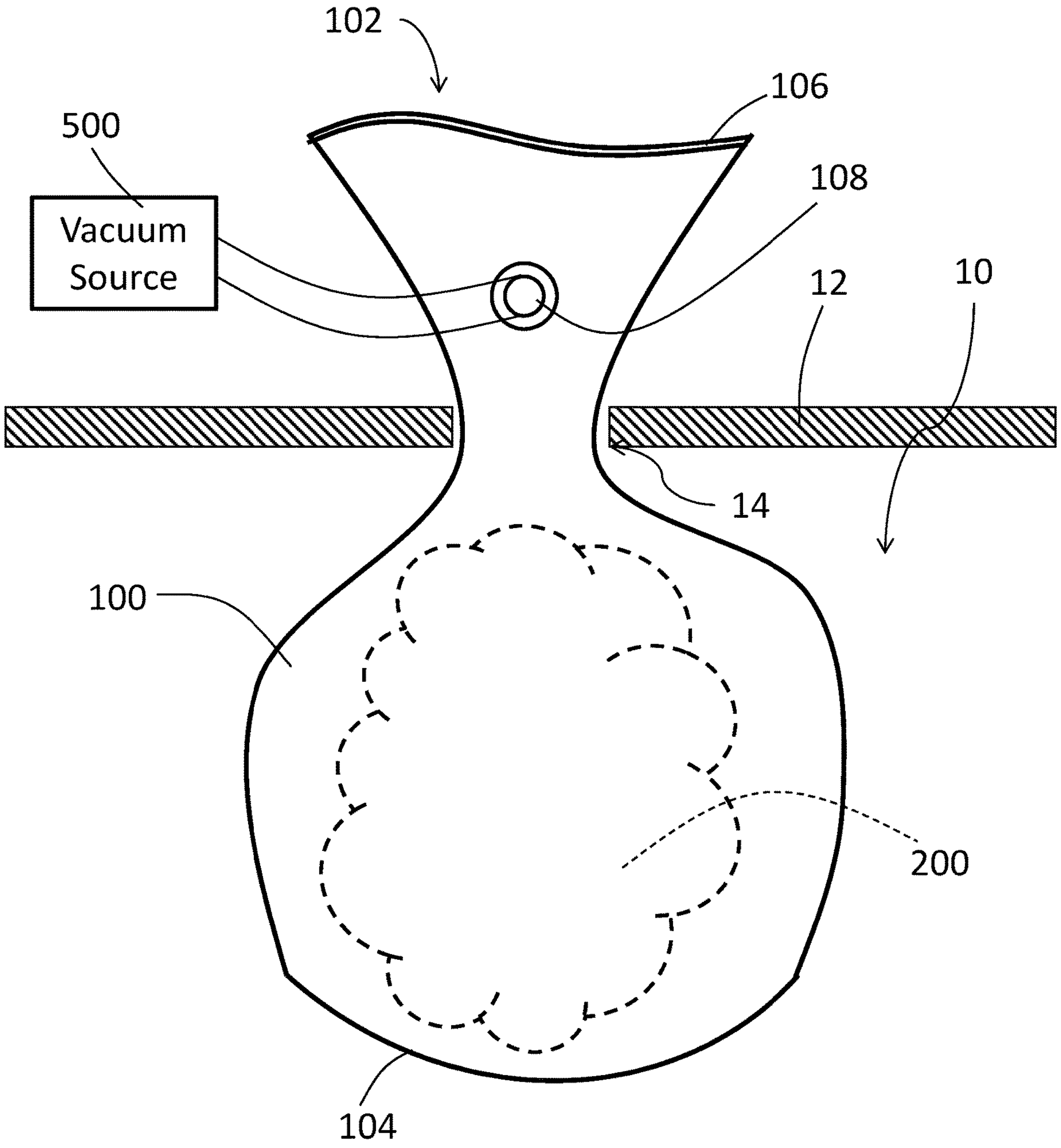
FIG. 7 shows the tissue specimen bag of FIG. 6 where a vacuum source has been coupled to the port according to one embodiment of the present invention.
Figure 8:
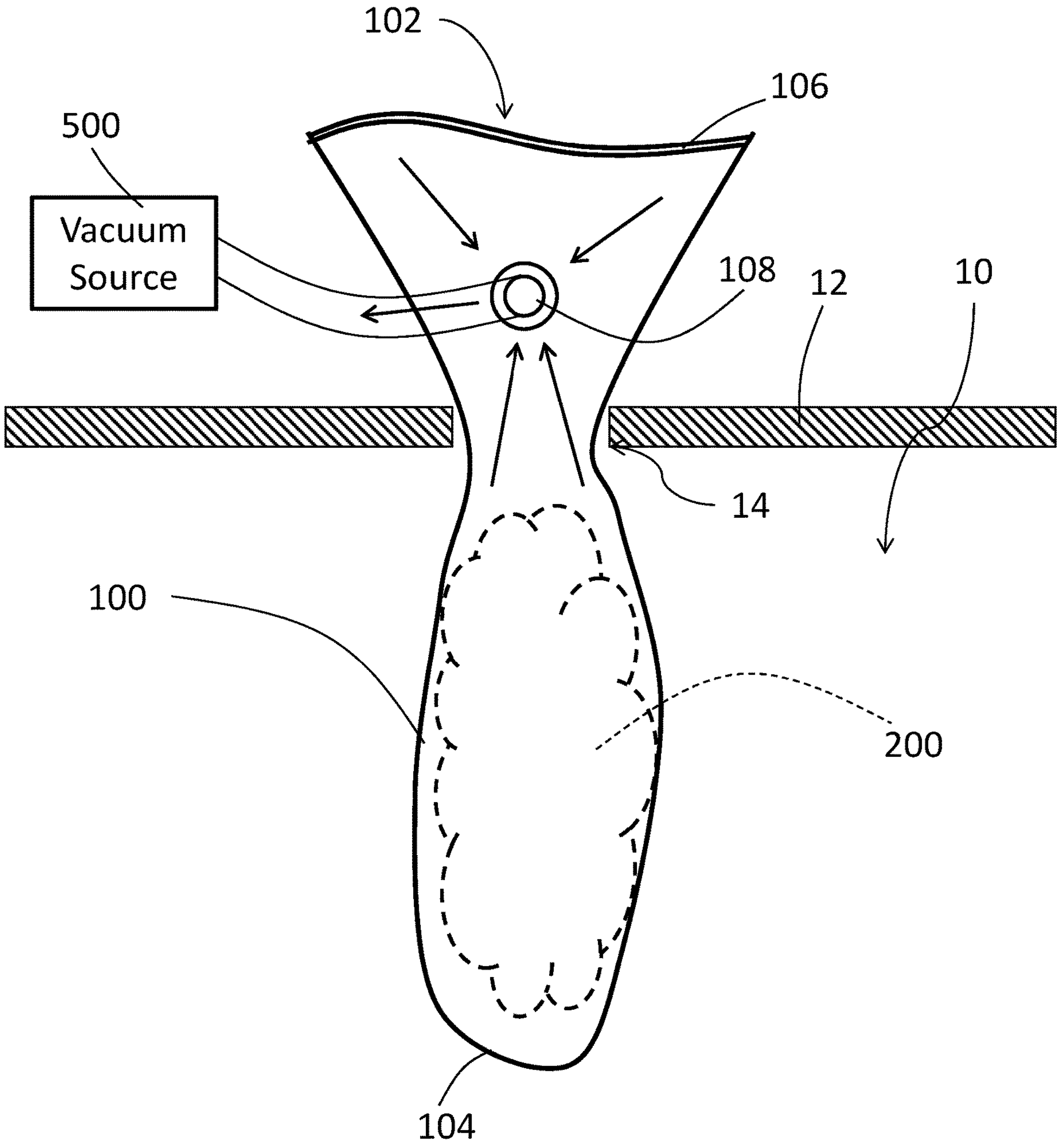
FIG. 8 shows the tissue specimen bag of FIG. 7 being deflated by the vacuum source according to one embodiment of the present invention.

With reference now to FIGS. 7 and 8, after open end 102 has been hermetically sealed, gas may be removed from the interior of bag 100 through port 108. In some embodiments, a vacuum source 500 may be coupled with port 108 in order to suction gas from the interior of bag 100 through port 108. In some embodiments, vacuum source 500 is coupled with port 108 on the exterior of bag 100. Vacuum source 500 may include, for example, a hand-held vacuum gun or other suitable suctioning device known in the art. In other embodiments, liquids (e.g., blood or other bodily fluids) that may be contained in bag 100 can also be withdrawn through port 108 by vacuum source 500. A liquid trap (not shown) may be provided to collect any liquids removed through port 108 according to some embodiments. In some embodiments, only gas is removed from bag 100 during the suctioning. In some embodiments, no portion of the suctioning device is inserted into the interior of bag 100. In some embodiments, removing gas from the interior of bag 100 causes compression of bag 100 and tissue specimen 200 contained therein. For example, where tissue specimen 200 includes lung tissue, gas contained in the lung tissue can be evacuated during suctioning to cause collapse and compression of the lung tissue. In some embodiments, removing gas from the interior of bag 100 reduces the volume of tissue specimen 200 by at least 10%, by at least 20%, by at least 25%, by at least 30%, by at least 35%, by at least 40%, by at least 45%, by at least 50%, by at least 55%, by at least 60%, by at least 65%, by at least 70%, by at least 75%, or by at least 80%. Preferably, the volume of tissue specimen 200 is sufficiently reduced to allow for tissue specimen 200 within bag 100 to pass through incision 14 without having to enlarge incision 14 according to some embodiments. In some embodiments, however, where tissue specimen 200 cannot be sufficiently compressed by suctioning alone (e.g., where tissue specimen 200 contains very stiff or solid materials), enlargement of incision 14 may be necessary before bag 100 can be completely withdrawn from cavity 10.

Figure 9:
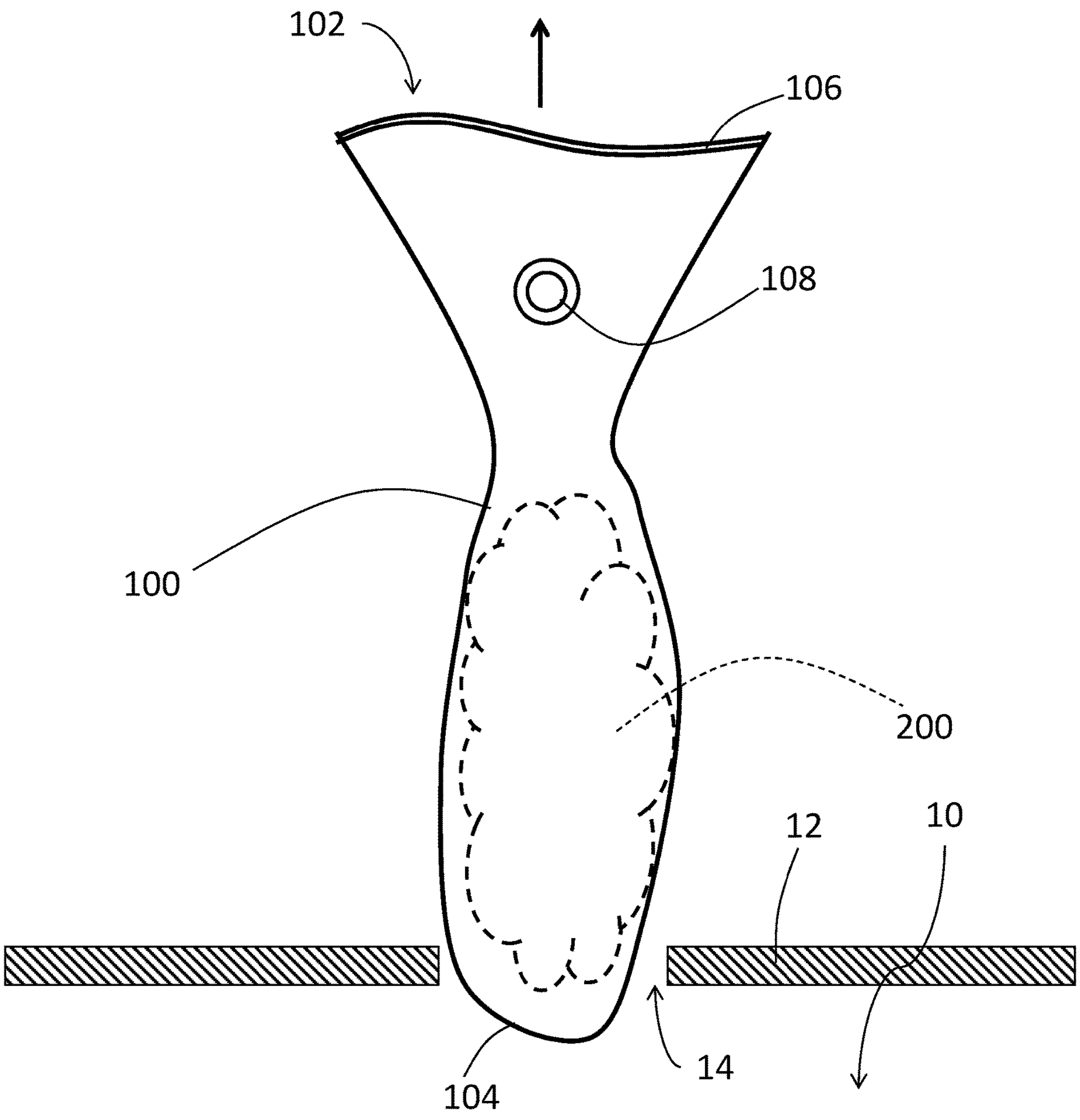
FIG. 9 shows the tissue specimen bag of FIG. 8 being withdrawn from the cavity through the incision according to one embodiment of the present invention.

FIG. 9 shows bag 100 containing tissue specimen 200 being withdrawn from cavity 10 through incision 14 after sufficient suctioning. Bag 100 may be pulled by hand out of cavity 10 through incision 14, according to some embodiments. In some embodiments, vacuum source 500 may be uncoupled from port 108 prior to entirely withdrawing bag 100 from cavity 10. In other embodiments, bag 100 may be completely withdrawn while vacuum source 500 is still coupled with port 108. As discussed above, in some embodiments port 108 includes a valve which is configured to prevent or at least retard gas from re-entering into the interior of bag 100 through port 108. The valve is preferably a one-way gas valve and may, for example, have any suitable configuration known in the art. The presence of a valve in port 108, in some embodiments, helps maintain bag 100 and tissue specimen 200 in the compressed state even while vacuum source 500 has been removed from port 108. In some embodiments, a cap or other component (not shown) may be provided to seal port 108 after suctioning to prevent further gas and/or liquid from passing through port 108. Once bag 100 and tissue specimen 200 is removed from cavity 10, tissue specimen 200 may be disposed of in any suitable manner or retained for later analysis. In some embodiments, closure device 106 may be unsealed to provide access to tissue specimen 200 after removal from the patient's body. In other embodiments, bag 100 may be cut or torn open to provide access to tissue specimen 200.

In further embodiments, a bag according to the present invention may include a spring element that is, for example, configured to facilitate opening of the bag during use inside the patient's body. Such a spring element may help ease insertion of the tissue specimen into the bag in some embodiments by helping to keep the open end of the bag open. In certain embodiments, the spring element may be removed from the bag after the tissue specimen has been inserted into the bag.

Figure 10:
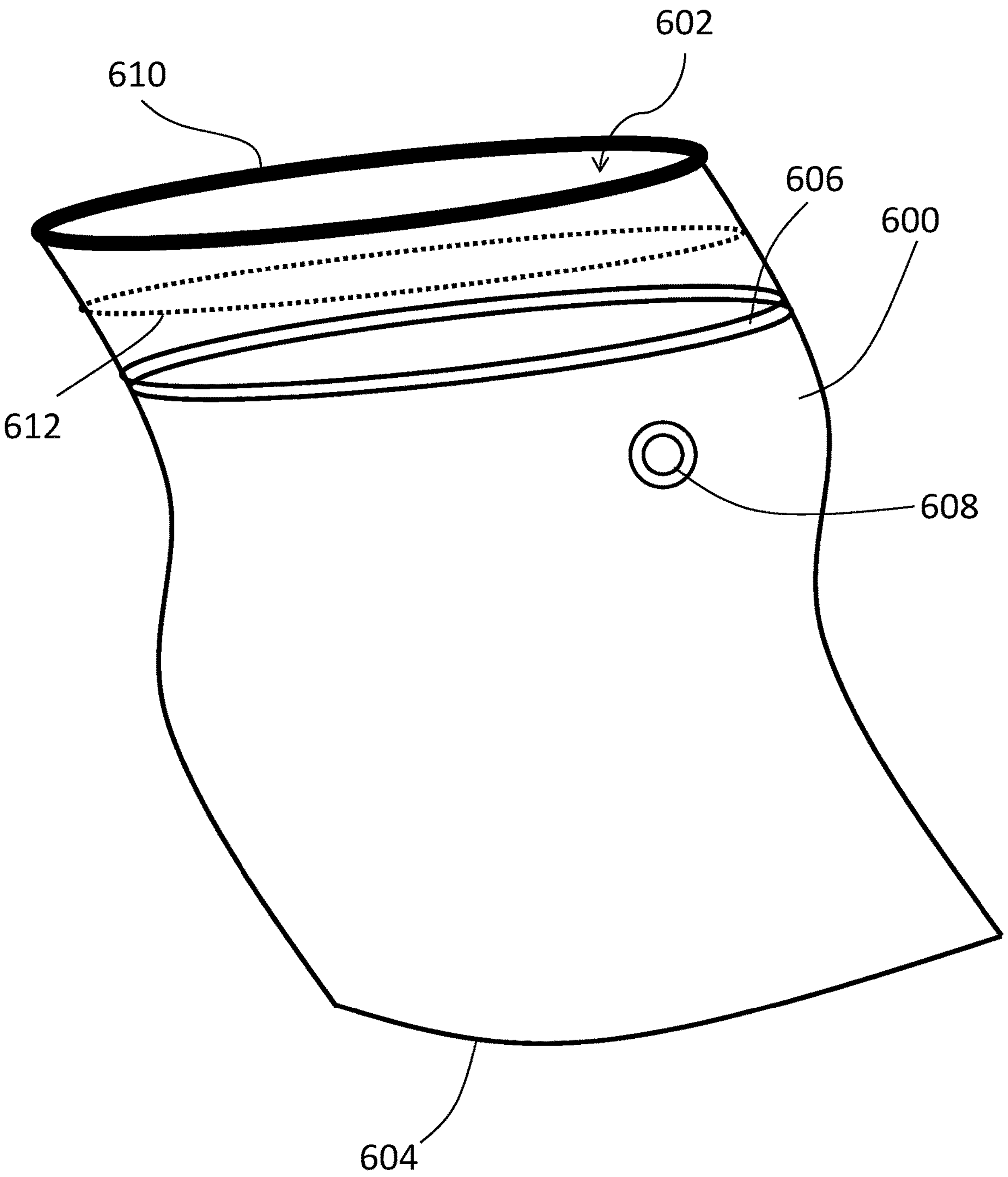
FIG. 10 shows a tissue specimen bag having a spring element at an open end according to a further embodiment of the present invention.

FIG. 10 shows a bag 600 having a spring element 610 which may be positioned at or proximate open end 602 according to one embodiment of the present invention. Spring element 610 may be attached to the exterior of bag 600, attached to the interior of bag 600, or positioned within the material which forms the walls of bag 600. In some embodiments, spring element 610 is not affixed to any additional tools. Bag 600, in some embodiments, further includes a closed end 604 that is opposite open end 602, a closure device 606 configured to seal bag 600, and a port 608 which may be analogous to and similarly configured as respective elements 104, 106, 108 described above in relation to bag 100. Other characteristics and features described above regarding bag 100 (e.g., materials, shape, sterilization, construction, etc.) may also be present in bag 600. In some embodiments, closure device 606 is situated between spring element 610 and closed end 604. In some embodiments, closure device 606 is positioned on bag 600 between spring element 610 and port 608. In yet further embodiments, bag 600 optionally includes a tear line 612 between closure device 606 and spring element 610 which may assist with removal of spring element 610 from bag 600 as will be described further below.

Spring element 610, in some embodiments, includes a resilient material that is shaped and configured to facilitate opening of bag 600 at open end 602. In some embodiments, spring element 610 is configured to cause open end 602 of bag 600 to spring open after insertion into the patient's body. In some embodiments, spring element 610 may be compressed to facilitate insertion of bag 600 into the body of the patient. According to some embodiments, spring element 610 may be shaped to have a generally curved configuration in an uncompressed state. In some embodiments, spring element 610 includes an elastic material that is formed into a loop or a portion of a loop that extends at least partially around open end 602 of bag 600. In some embodiments, spring element 610 extends around the entire open end 602 of bag 600. In other embodiments, spring element 610 extends only along a portion of open end 602 of bag 600. In some embodiments, for example, spring element 610 is made from an elastic wire or band that is formed into a compressible spring loop or portion thereof that at least partially extends around open end 602 of bag 600. In some embodiments, spring element 610 is made from an elastic metal or alloy (e.g., spring steel, shape memory alloy, etc.). In other embodiments, spring element 610 is made from an elastic plastic, polymer, or composite material. Preferably spring element 610 is made from a sterilizable material, e.g., a material which can withstand the sterilization process without degrading or substantial loss of elasticity.

Figure 11:
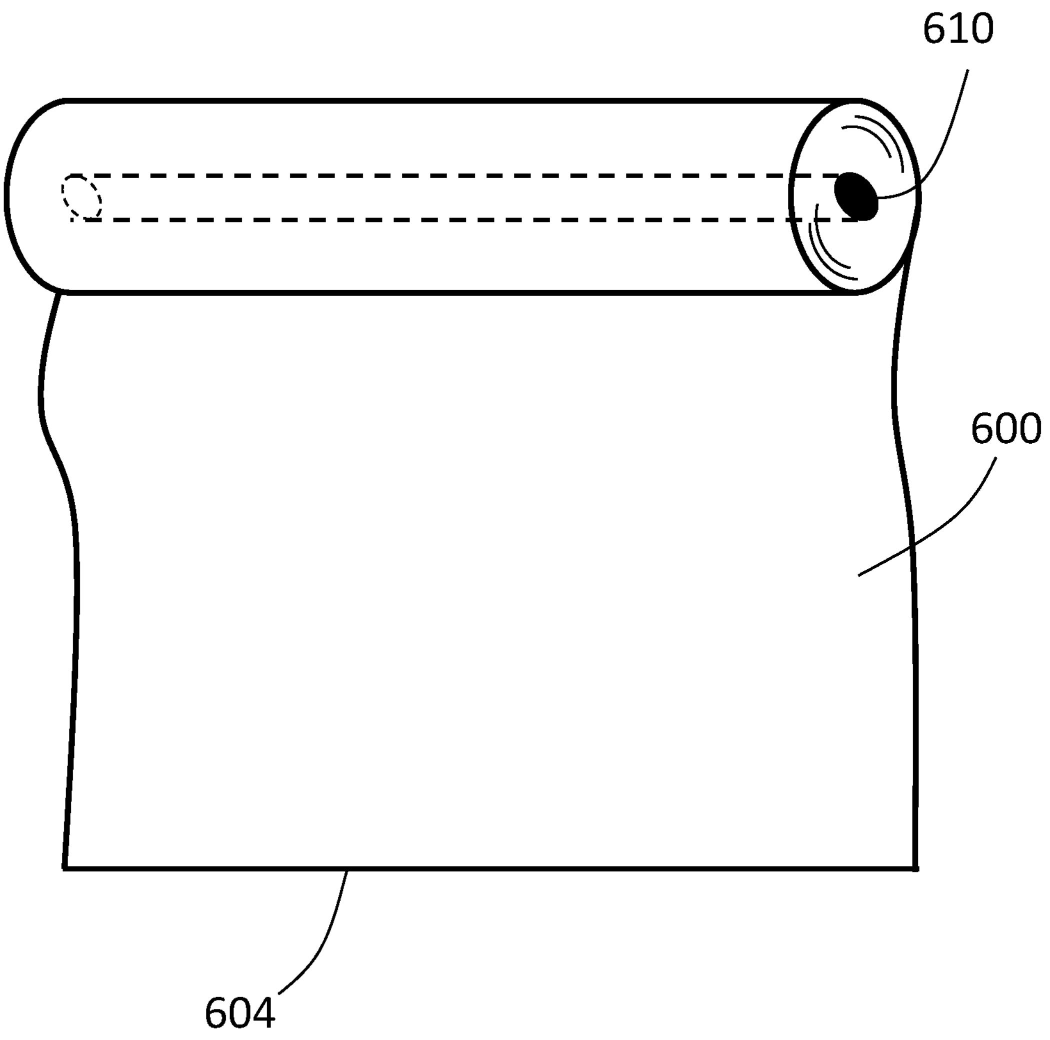
FIG. 11 shows the tissue specimen bag of FIG. 10 partially coiled around the spring element according to one embodiment of the present invention.

Referring now to FIG. 11, in some embodiments, spring element 610 may be compressed to allow for the remainder of bag 600 to be coiled around spring element 610 as illustrated. In some embodiments, coiling bag 600 facilitates insertion of bag 600 into the patient's body by making bag 600 more compact. In some embodiments, bag 600 in the coiled configuration may be further packaged in a sterile sleeve (e.g., sleeve 300 described above) that in turn may be used to introduce bag 600 through an incision and into a cavity in the patient's body.

Figure 12:
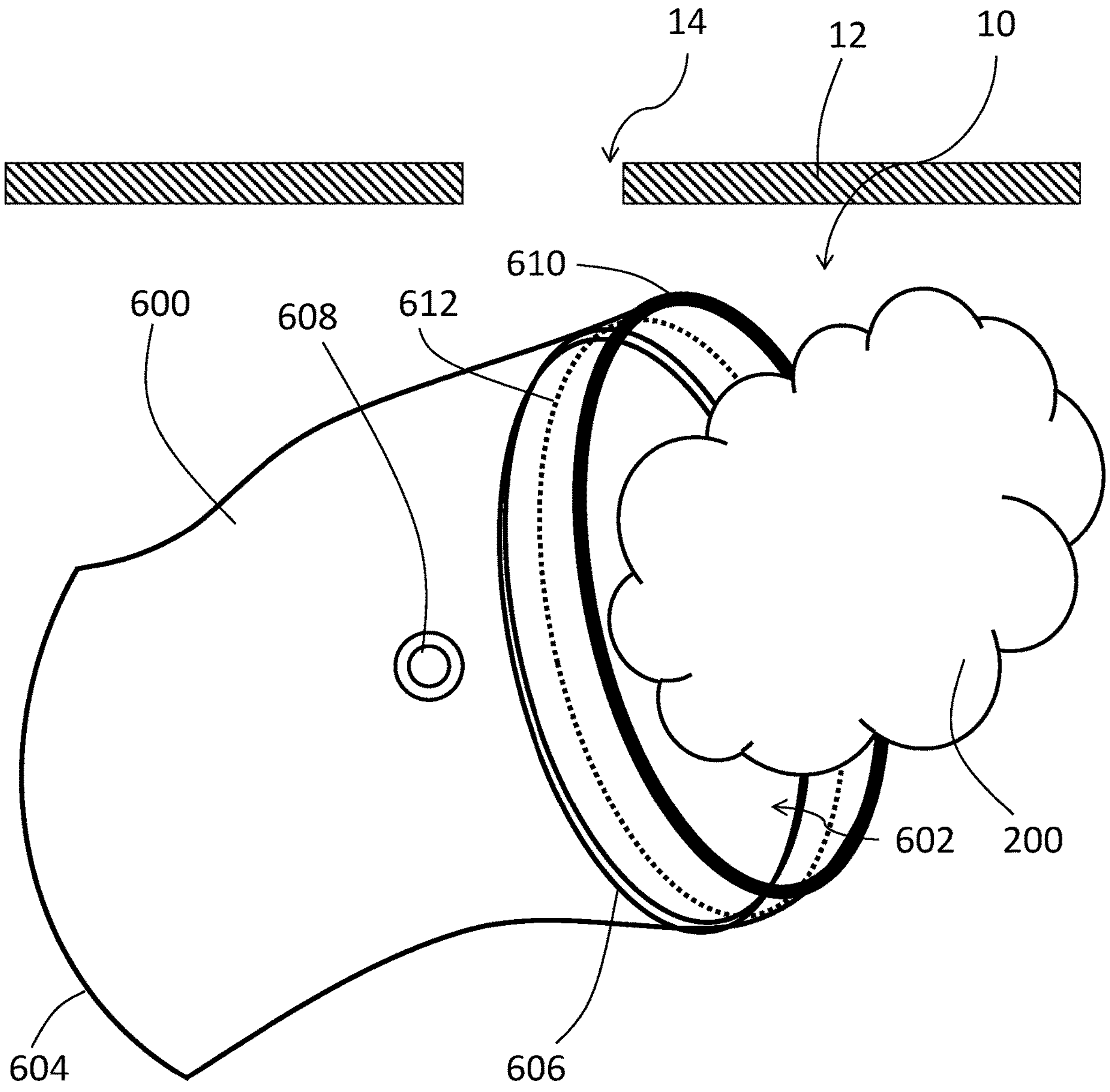
FIG. 12 shows a tissue specimen passing through the open end of the specimen bag of FIG. 10 according to one embodiment of the present invention.
Figure 13:
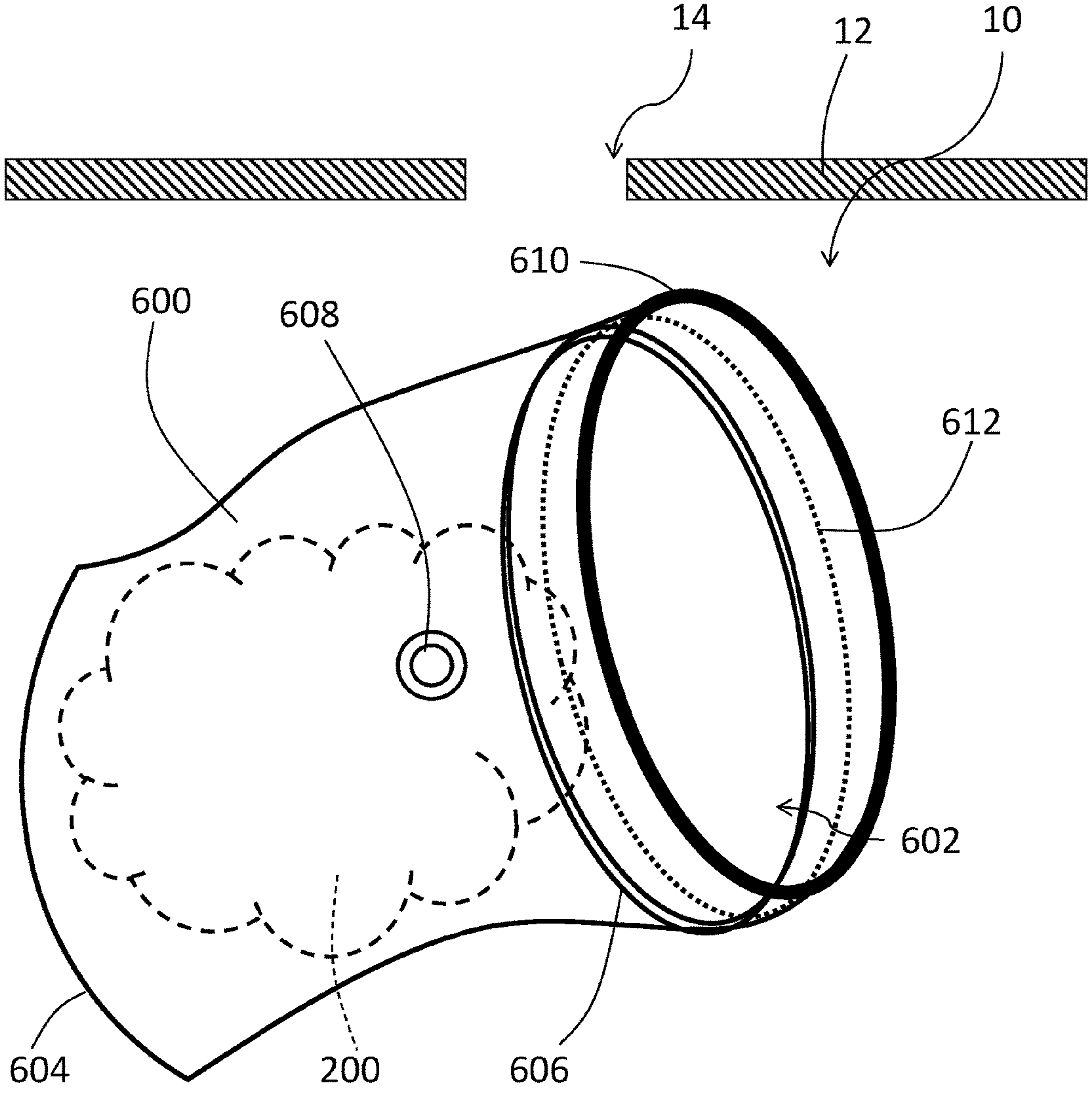
FIG. 13 shows the tissue specimen of FIG. 12 fully positioned within the interior of the tissue specimen bag according to one embodiment of the present invention.

FIG. 12 shows bag 600 after insertion into cavity 10 through an incision 14 in a body wall 12 according to one embodiment. Once inserted into cavity 10, bag 600 may be uncoiled within cavity 10. In some embodiments, the spring force of spring element 610 is sufficient to cause bag 600 to uncoil at least partially. In some embodiments, spring element 610 further causes open end 602 of bag 600 to spring open due to its elastic nature. In some embodiments, uncoiling of bag 600 and/or opening of open end 602 may be assisted with the use of one or more separate tools (not shown), for example, laparoscopic forceps. As discussed above, in some embodiments, spring element 610 is configured to help keep open end 602 open while bag 600 is positioned within cavity 10. By keeping open end 602 open during use, it may be easier for the surgeon to place tissue specimen 200 into bag 600, as illustrated in FIG. 13.

Figure 14:
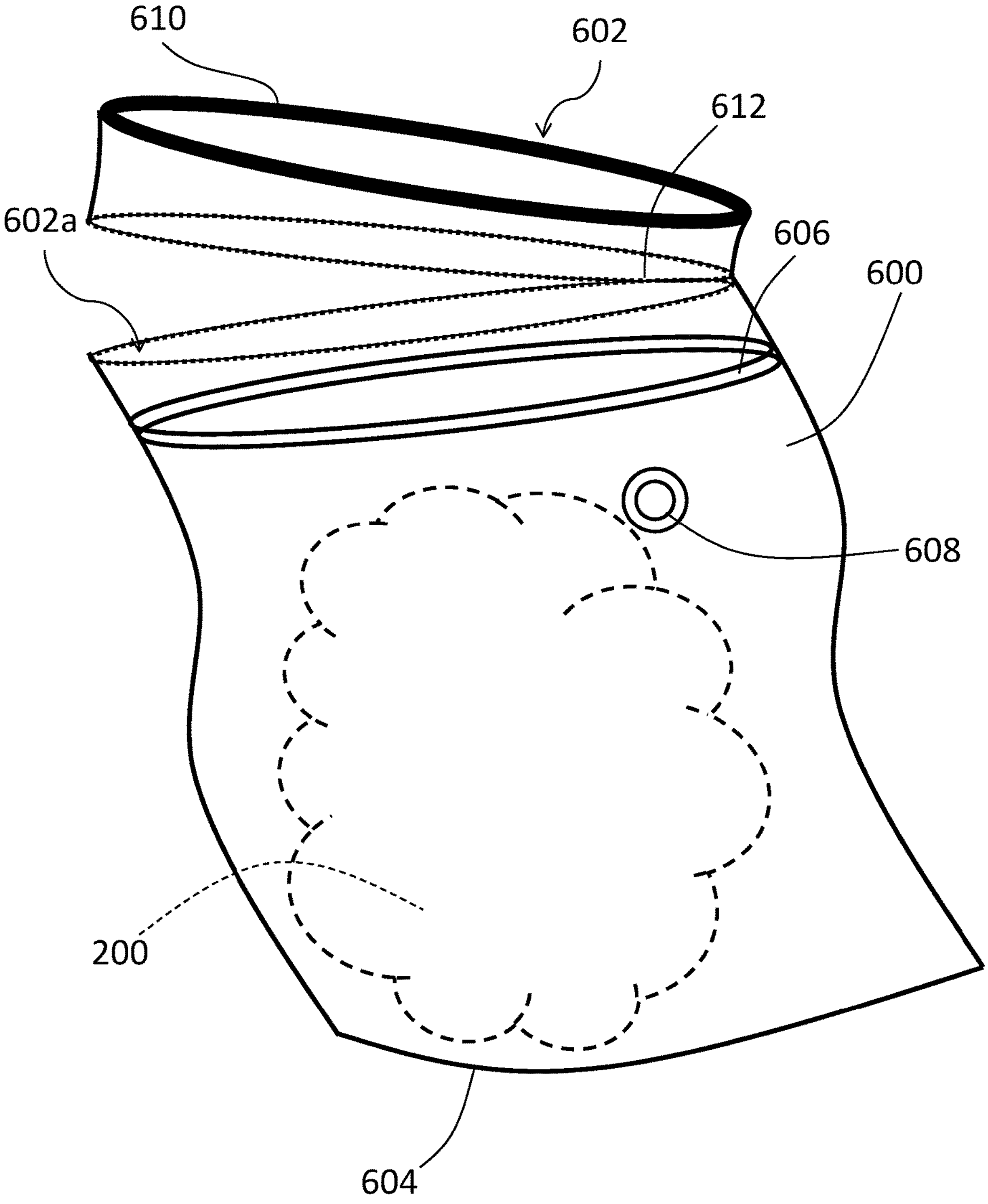
FIG. 14 shows the tissue specimen bag of FIG. 13 with the spring element being separated from the open end according to one embodiment of the present invention.

In some embodiments, after tissue specimen 200 has been positioned within bag 600, spring element 610 may be separated from bag 600. In some embodiments, spring element 610 is removed from bag 600 to allow for closure device 606 to seal bag 600. In some embodiments, open end 602 of bag 600 may be withdrawn from cavity 10 prior to separating spring element 610 from bag 600. In other embodiments, spring element 610 may be separated from bag 600 while inside cavity 10 and then subsequently withdrawn from cavity 10 (e.g., using forceps). FIG. 14 shows spring element 610 being separated from bag 600 according to one embodiment of the present invention. According to this embodiment, bag 600 optionally includes tear line 612 situated between spring element 610 and closure device 606 and which is configured to allow spring element 610 to be torn away from the portion of bag 600 containing tissue specimen 200. In some embodiments, tear line 612 allows spring element 610 to be torn away without the need for additional or specialized tools. In some embodiments, for example, tear line 612 is a line of perforations on the walls of bag 600. In some embodiments, tear line 612 is a groove or scored line where the thickness of the walls of bag 600 may be reduced in order to facilitate tearing. In other embodiments, spring element 610 may be cut from bag 600 using a cutting tool (e.g., scalpel, knife, scissors, etc.). The cutting tool may be used to cut bag 600 between spring element 610 and closure device 606 to separate spring element 610 from the remainder of bag 600, however care should be taken to avoid cutting or puncturing bag 600 anywhere between closure device 606 and closed end 604. As shown in FIG. 14, a portion of bag 600 which originally included open end 602 may be separated along with spring element 610. For ease of explanation, open end 602*a* represents the open end of bag 600 following the separation and removal of spring element 610 and may be located where bag 600 was torn or cut. After separation of spring element 610 from bag 600, the use of bag 600 may follow the same procedure described above with respect to bag 100 shown in FIGS. 5-9.

In some embodiments, following separation of spring element 610 from bag 600, closure device 606 may be closed to seal bag 600 in a manner similar to that described for closure device 106 of bag 100 above. In some embodiments, closure device 606 is withdrawn from cavity 10 (e.g., through incision 14) prior to closing closure device 606. In some embodiments, closure device 606 is particularly configured to hermetically seal bag 600. In some embodiments, closure device 606 includes interlocking components, for example, a zipper closure. Closure device 606 may be configured to be closed by hand to form a hermetic seal without the use of additional tools or binders according to some embodiments. In some embodiments, closure device 606 is capable of being unsealed and resealed such that bag 600 may be reopened and resealed if needed. In other embodiments, open end 602*a* may be permanently sealed such that bag 600 must be cut or torn to open bag 600. In some such embodiments, for example, open end 602*a* may be heat sealed. In yet other embodiments, open end 602*a* may be sealed with adhesive (e.g., cyanoacrylate glue).

Figure 15:
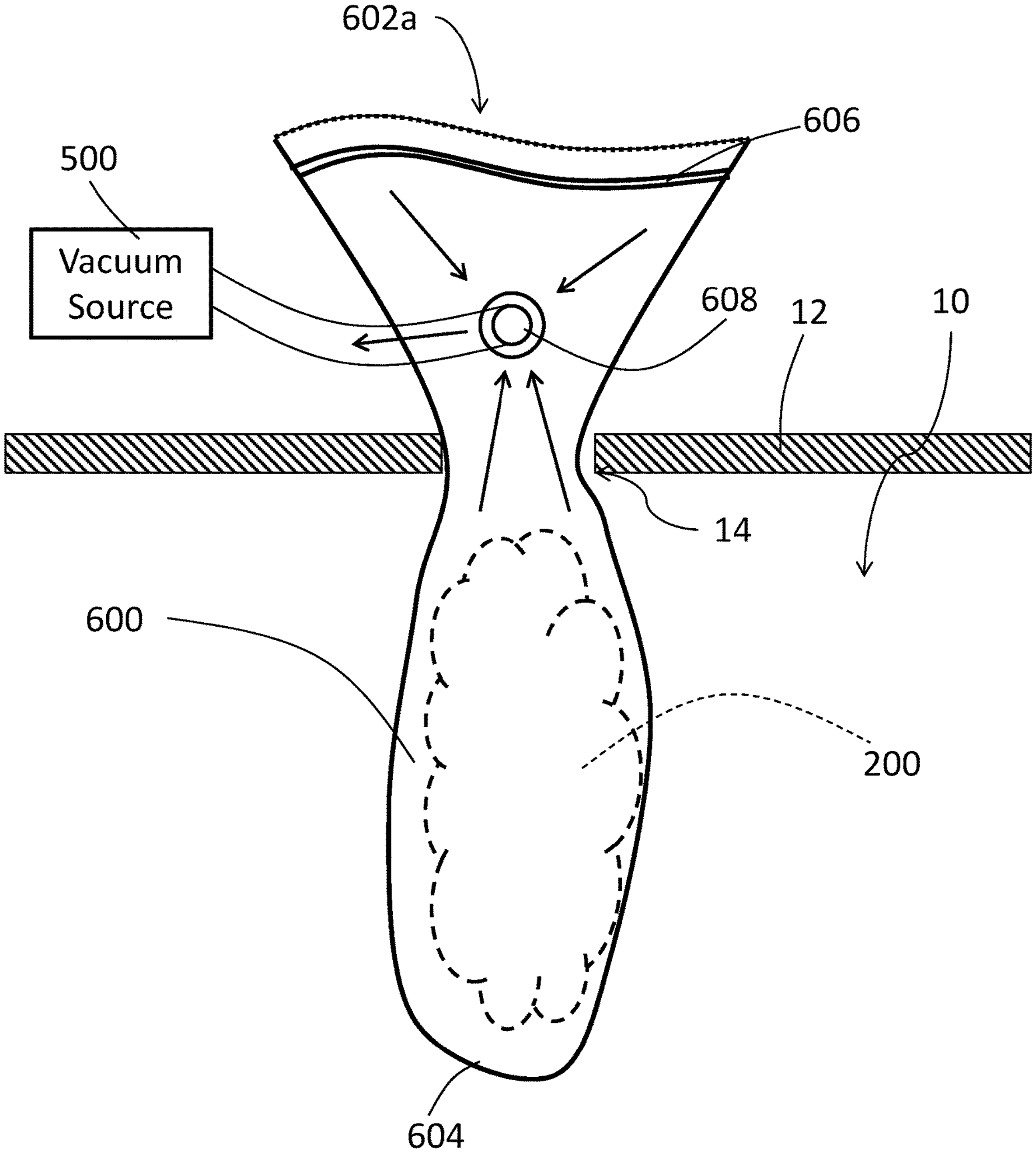
FIG. 15 shows the tissue specimen bag of FIG. 14 where a vacuum source has been coupled to the port according to one embodiment of the present invention.

Similar to the procedure described above with regards to bag 100, after bag 600 has been hermitically sealed, gas may be removed from the interior of bag 600 through port 608. As shown in FIG. 15, in some embodiments a vacuum source 500 may be coupled with port 608 in order to suction gas from the interior of bag 100 through port 608. In some embodiments, port 608 has been withdrawn from cavity 10 (e.g., through incision 14) prior to coupling vacuum source 500 with port 608. In some embodiments, vacuum source 500 is coupled with port 608 on the exterior of bag 600. Vacuum source 500 may include, for example, a hand-held vacuum gun or other suitable suctioning device known in the art. In other embodiments, liquids (e.g., blood or other bodily fluids) that may be contained in bag 600 can also be withdrawn through port 608 by vacuum source 600. A liquid trap (not shown) may be provided to collect any liquids removed through port 608 according to some embodiments. In some embodiments, only gas is removed from bag 600 during the suctioning. In some embodiments, no portion of the suctioning device is inserted into the interior of bag 600. In some embodiments, removing gas from the interior of bag 600 causes compression of bag 600 and tissue specimen 200 contained therein. For example, where tissue specimen 200 includes lung tissue, gas contained in the lung tissue can be evacuated during suctioning to cause collapse and compression of the lung tissue. In some embodiments, removing gas from the interior of bag 600 reduces the volume of tissue specimen 200 by at least 10%, by at least 20%, by at least 25%, by at least 30%, by at least 35%, by at least 40%, by at least 45%, by at least 50%, by at least 55%, by at least 60%, by at least 65%, by at least 70%, by at least 75%, or by at least 80%. Preferably, the volume of tissue specimen 200 is sufficiently reduced to allow for tissue specimen 200 within bag 600 to pass through incision 14 without having to enlarge incision 14 according to some embodiments. In some embodiments, however, where tissue specimen 200 cannot be sufficiently compressed by suctioning alone (e.g., where tissue specimen 200 contains very stiff or solid materials), enlargement of incision 14 may be necessary before bag 600 can be completely withdrawn from cavity 10.

Once bag 600 containing tissue specimen 200 has been sufficiently compressed to pass through incision 14, bag 600 may be pulled by hand out of cavity 10 through incision 14, according to some embodiments. In some embodiments, vacuum source 500 may be uncoupled from port 608 prior to entirely withdrawing bag 600 from cavity 10. In other embodiments, bag 600 may be completely withdrawn while vacuum source 500 is still coupled with port 608. As with port 108 of bag 100, in some embodiments port 608 includes a valve which is configured to prevent or at least retard gas from re-entering into the interior of bag 600 through port 608. The valve is preferably a one-way gas valve and may, for example, have any suitable configuration known in the art. The presence of a valve in port 608, in some embodiments, helps maintain bag 600 and tissue specimen 200 in the compressed state even while vacuum source 500 has been removed from port 608. In some embodiments, a cap or other component (not shown) may be provided to seal port 608 after suctioning to prevent further gas and/or liquid from passing through port 608. Once bag 600 and tissue specimen 200 is removed from cavity 10, tissue specimen 200 may be disposed of in any suitable manner or retained for later analysis. In some embodiments, closure device 606 may be unsealed to provide access to tissue specimen 200 after removal from the patient's body. In other embodiments, bag 600 may be cut or torn open to provide access to tissue specimen 200.

In certain embodiments, a bag for use according to the present invention (e.g., bag 100, 600) does not need to have an integral closure device (e.g., a zipper closure) for hermetically sealing the open end of the bag. In some such embodiments, the open end of the bag may instead be hermetically sealed with tape, sutures, ties, elastic bands, or other binding material. In other such embodiments, a device which is separate from the bag, such as a separate clamping device may be used to close and hermetically seal the open end of the bag.

Figure 16A:
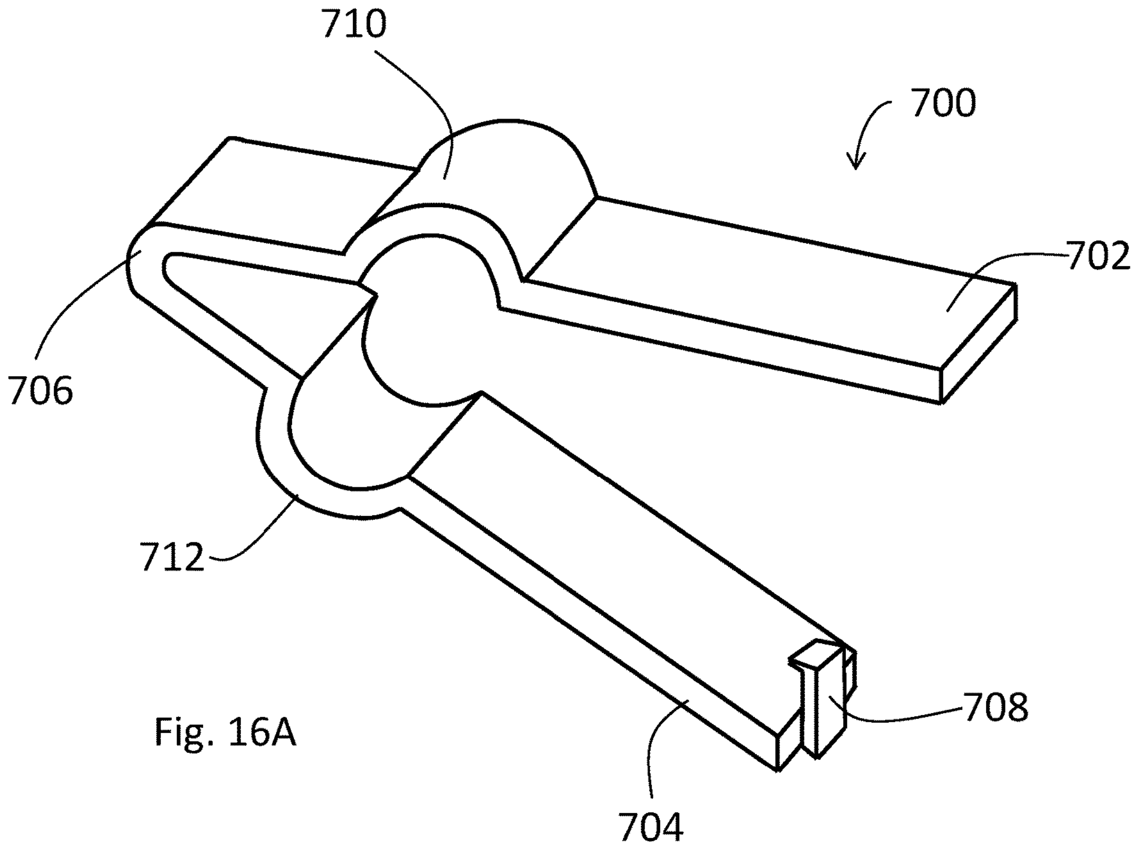
FIG. 16A shows a perspective view of a clip for a tissue specimen bag according to a further embodiment of the present invention in an open configuration.
Figure 16B:
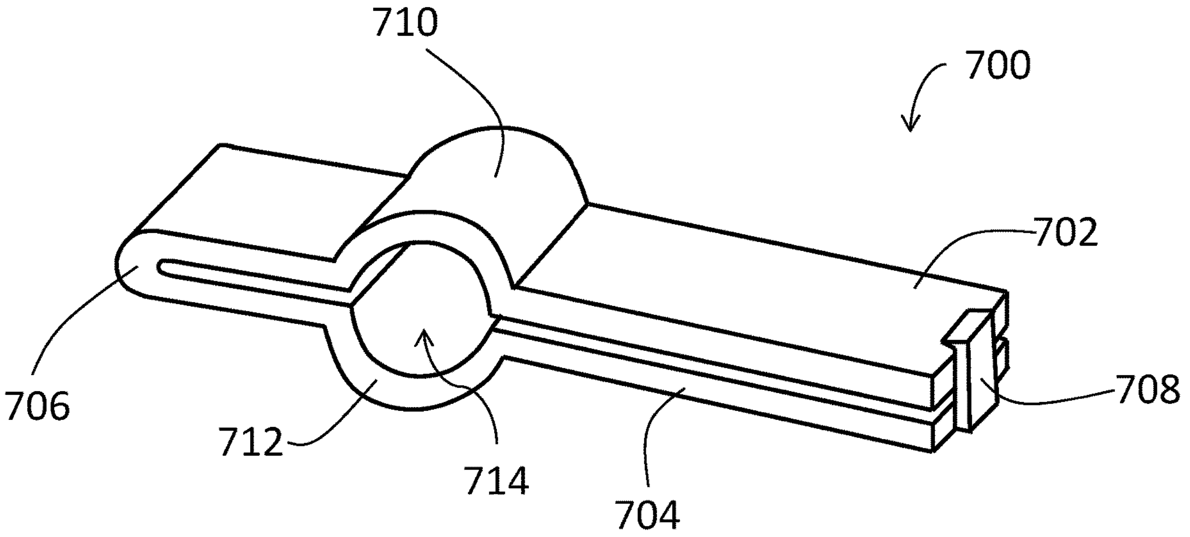
FIG. 16B shows a perspective view of the clip of FIG. 16A in a closed configuration.
Figure 17A:
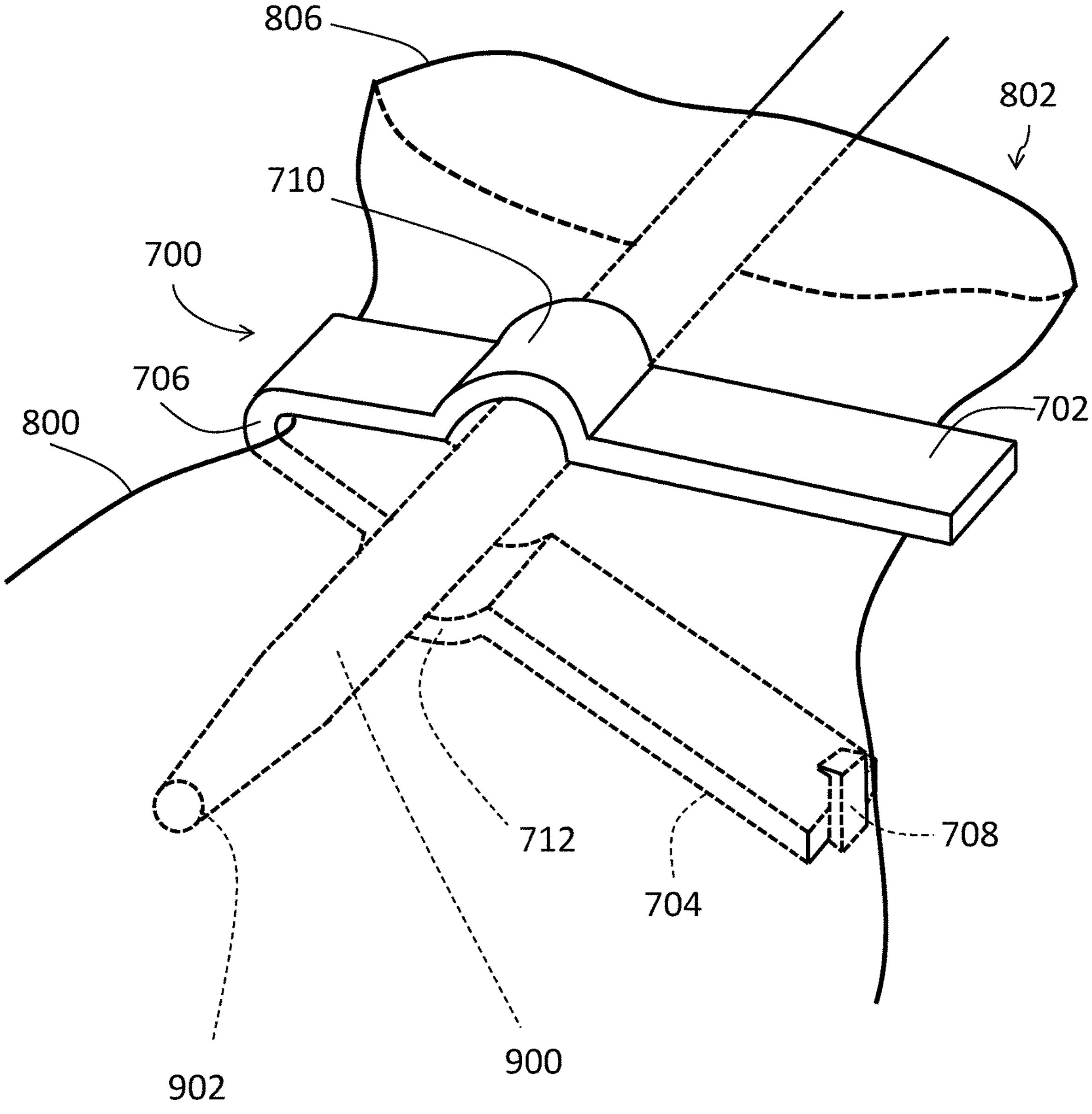
FIG. 17A shows the clip of FIG. 16A in the open configuration being positioned around a tissue specimen bag and a suction device according to one embodiment of the present invention.
Figure 17B:
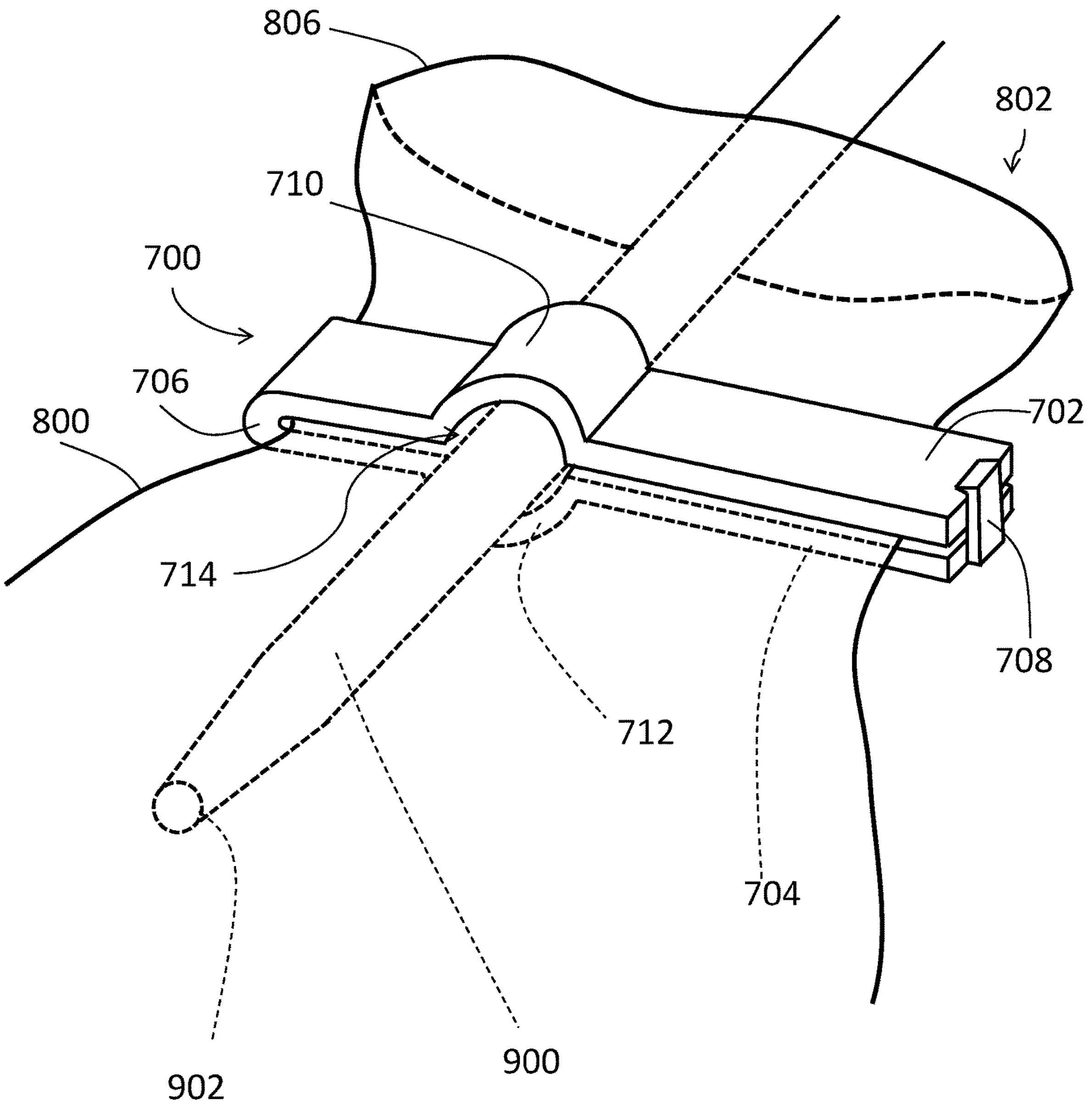
FIG. 17B shows the clip of FIG. 17A in a closed configuration around the tissue specimen bag and the suction device.
Figure 18A:
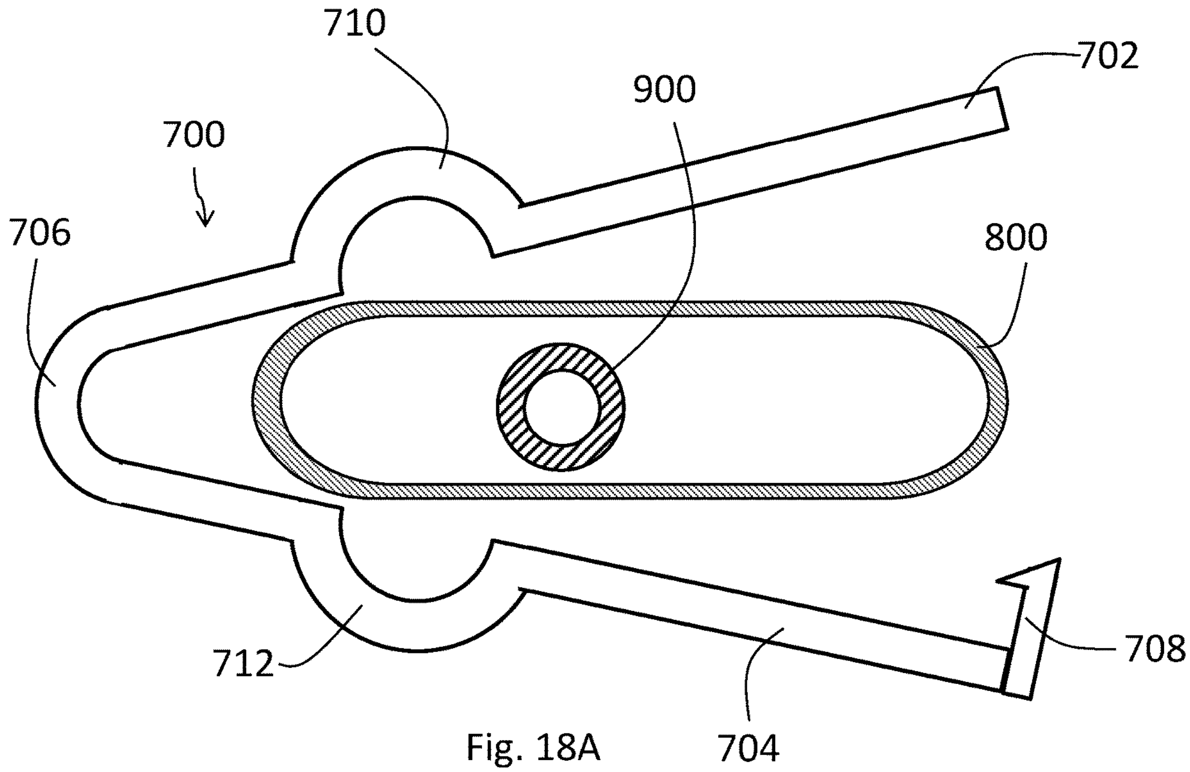
FIG. 18A shows a cross-sectional view of the clip of FIG. 16A in the open configuration being positioned around a tissue specimen bag and a suction device according to one embodiment of the present invention.
Figure 18B:
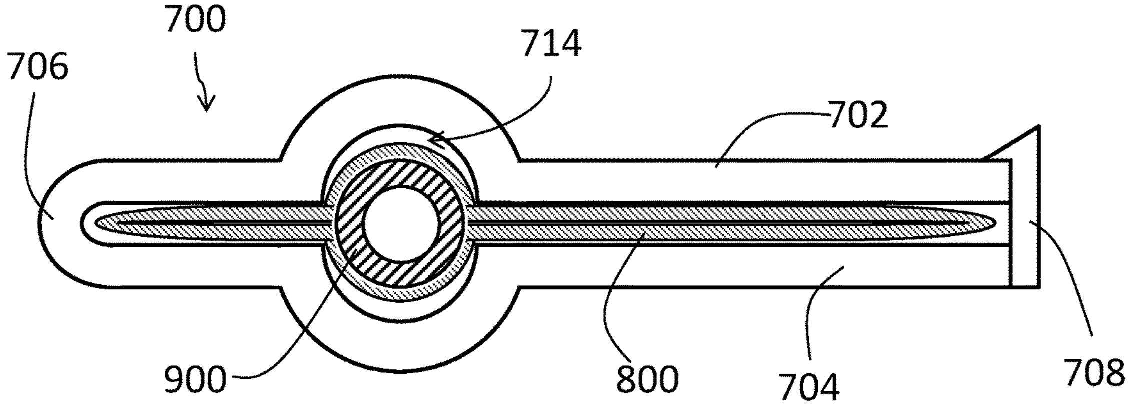
FIG. 18B shows a cross-sectional view of the clip of FIG. 16A in a closed configuration around the tissue specimen bag and the suction device.

The present invention, according to some embodiments, provides a clip which may be used to hermetically seal a bag that does not necessarily have an integral closure device capable of hermetically sealing the bag, e.g., certain conventional specimen bags. In some embodiments, a clip according to the present invention may be particularly configured to hermetically seal the bag while a suction device is inserted into the interior of the bag through the opening of the bag. One such example is illustrated in FIGS. 16A-18B, which shows a clip 700 which may be used to hermetically seal a bag 800 according to certain embodiments of the present invention. Clip 700, in some embodiments, includes a first leg 702 and a second leg 704 which are movable with respect to each other between an open configuration (FIGS. 16A, 17A, 18A) and a closed configuration (FIGS. 16B, 17B, 18B). Bag 800 may be received between first and second legs 702, 704 in the open configuration (FIGS. 17A, 18A). In the closed configuration, according to some embodiments, first leg 702 and second leg 704 are configured to clamp against the walls of bag 800 in order to form a hermetically seal at a portion of bag 800.

In some embodiments, first leg 702 and second leg 704 are connected to each other by a hinge portion 706 which may be configured as any sort of hinge capable of allowing first and second legs 702, 704 to pivot towards or away from each other. In some embodiments, for example, hinge portion 706 may include a pin about which first and second legs 702, 704 rotate. In other embodiments, hinge portion 706 may be a living hinge wherein hinge portion 706 is a flexible area between first and second legs 702, 704. In some embodiments, first and second legs 702, 704 are separate pieces which are connected by hinge portion 706. In other embodiments, first and second legs 702, 704 and hinge portion 706 are integrally formed from a single piece of material. First and second legs 702, 704 may be made from any materials suitable for securely clamping against bag 800, for example, metals, plastics, polymers, composite materials, etc. In some embodiments, first and second legs 702, 704 are rigid or substantially rigid. In some embodiments, first and second legs 702, 704 may have a degree of flexibility. In certain embodiments, for example where clip 700 is used for tissue specimen removal, clip 700 is sterilized. In some embodiments, clip 700 may be further provided with an anti-microbial substance or coating.

In further embodiments, clip 700 may further include a closure 708 which is configured to maintain first and second legs 702, 704 in the closed configuration. In some embodiments, closure 708 may be configured as a latch, hook, snap fitting, or any other suitable mechanical feature capable of securing first leg 702 relative to second leg 704 in the closed configuration. In some embodiments, closure 708 may include a protrusion which extends from one of first leg 702 or second leg 704 (as illustrated) and which is configured to contact and engage with the other leg in the closed configuration. In some embodiments, closure 708 may include a first feature on first leg 702 (e.g., hook) which engages with a second feature (e.g., loop) on second leg 704 to secure first and second legs 702, 704 together. In some embodiments, closure 708 includes features on first and second legs 702, 704 which are configured to interlock. In some embodiments, closure 708 may be positioned at or proximate a free end of first leg 702 and/or second leg 704 which is opposite hinge portion 706. In other embodiments, closure 708 may include a device separable from clip 700. For example, in some embodiments, closure 708 may include a separate clamping device or fastener which may be applied to first and second legs 702, 704 in the closed configuration.

In some embodiments, clip 700 is configured to hermetically seal bag 800 while a suction device is inserted into the interior of bag 800. Clip 700, for example, may be configured to hermetically seal bag 800 around and/or against the suction device. In some embodiments, clip 700 provides a clearance (e.g., a gap, aperture, or opening) between first and second legs 702, 704 in the closed configuration which is sized to receive the suction device. In the illustrated embodiments, for example, first leg 702 includes a first collar portion 710 and second leg 704 includes a second collar portion 712 which together define an opening 714 that may be shaped and sized to receive a suction device 900 in the closed configuration (FIG. 17B, 18B). In some embodiments, at least one of first leg 702 and second leg 704 includes a concavely curved internal surface which at least partially defines opening 714. Suction device 900, may be, for example, a hollow suction catheter connected to a vacuum source and extending into the interior of bag 800 through open end 802 of bag 800. Suction device 900 may include a tip 902 positioned in the interior of bag 800 and be configured for removing gas from the interior of bag 800. In some embodiments, opening 714 is shaped and sized to hermetically seal bag 800 against or around a portion of suction device 900. First and second collar portions 710, 712 may have internal surfaces that are concavely curved to define the shape and size of opening 714. For example, first and second collar portions 710, 712 may have semicircular internal surfaces such that opening 714 is generally circular according to some embodiments, though other shapes may also be utilized in other embodiments. In some embodiments, first and second collar portions 710, 712 make up only a portion of first and second legs 702, 704. In some embodiments, first and second collar portions 710, 712 comprise less than half, less than a third, or less than a fourth of the length of first and second legs 702, 704. As shown in FIGS. 16A-18B, other portions of first and second legs 702, 704 may be generally planar according to some embodiments, though they are not necessarily limited to this shape. Moreover, while in the illustrated embodiments first and second collar portions 710, 712 are shown to be closer to hinge portion 706 than to closure 708, it should be understood that first and second collar portions 710, 712 may be positioned at other locations along first and second legs 702, 704, for example, at the middle of first and second legs 702, 704, or proximate closure 708.

Figure 19:
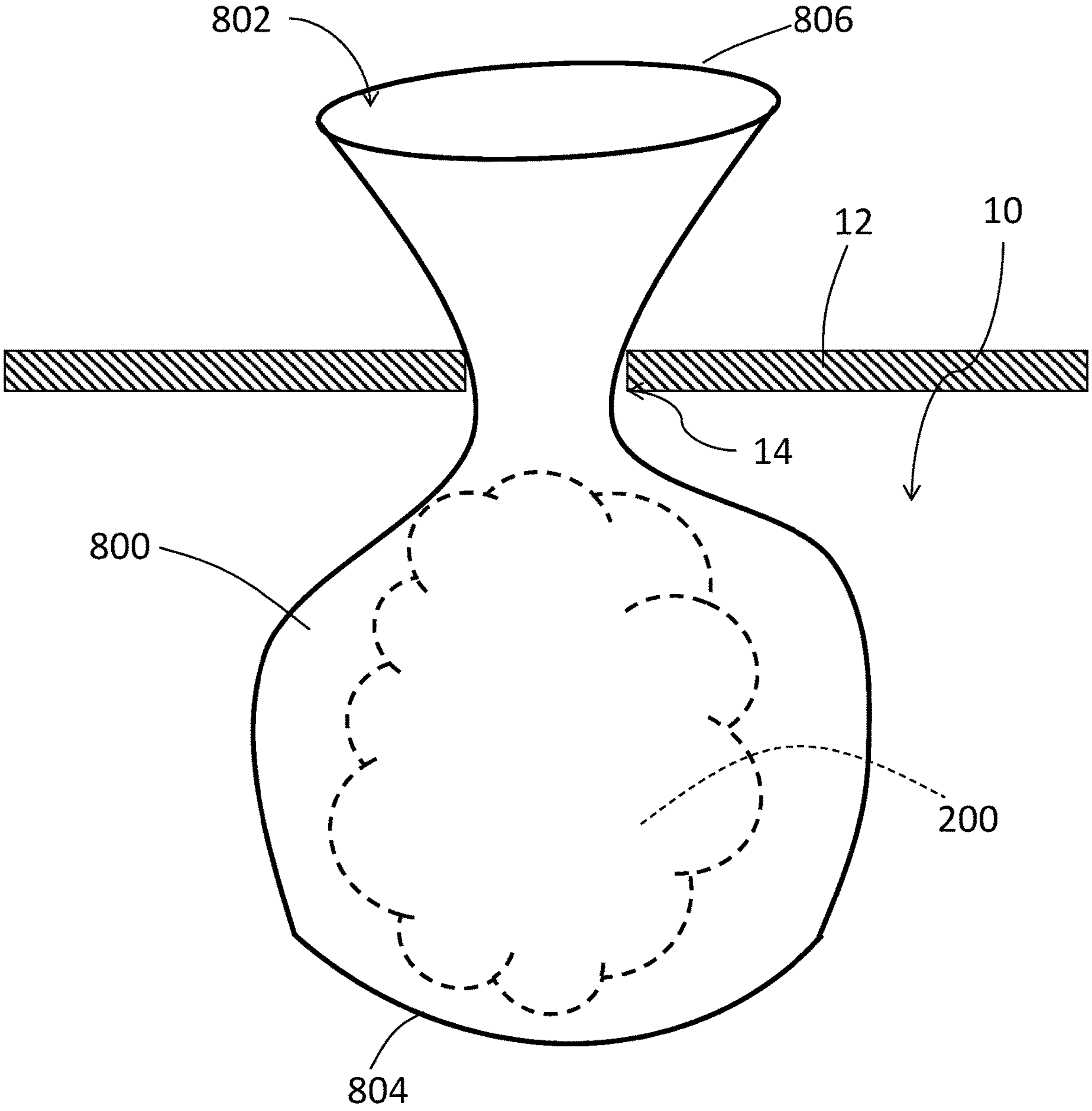
FIG. 19 shows a tissue specimen within the interior of a tissue specimen bag which is partially positioned within a cavity of a patient according to one embodiment of the present invention.

With reference now to FIGS. 19-23, a use of clip 700 in the removal of a tissue specimen according to an embodiment of the present invention will now be described. FIG. 19 shows bag 800 containing a tissue specimen 200 and positioned partially within cavity 10. Cavity 10 may, for example, be a thoracic cavity of the patient, body wall 12 may represent the chest wall, and tissue specimen 200 may represent a portion of lung tissue which has been cut from the patient. Similar to the embodiments described above with respect to bags 100, 600, bag 800 may have been introduced and into cavity 10 through incision 14 using a sterile sleeve (e.g., sterile sleeve 300 previously described). Other techniques known in the art for introducing a specimen bag into a body cavity may also be used in other embodiments. In particular, open end 802 of bag 800 has been withdrawn from cavity 10 through incision 14 while closed end 804 and a portion of bag 800 containing tissue specimen 200, which may be too large to fit through incision 14, remains within cavity 10. Bag 800 may be generally configured similar to bags 100, 600 described above. Unlike bags 100, 600, bag 800 may not include any ports (e.g., ports 108, 608) and may not include a closure device at open end 802 according to some embodiments. In some embodiments, bag 800 may be a conventional tissue specimen bag. In further embodiments, bag 800 may include a drawstring closure at rim 806, but the drawstring closure may not be configured to hermetically seal bag 800.

Figure 20:
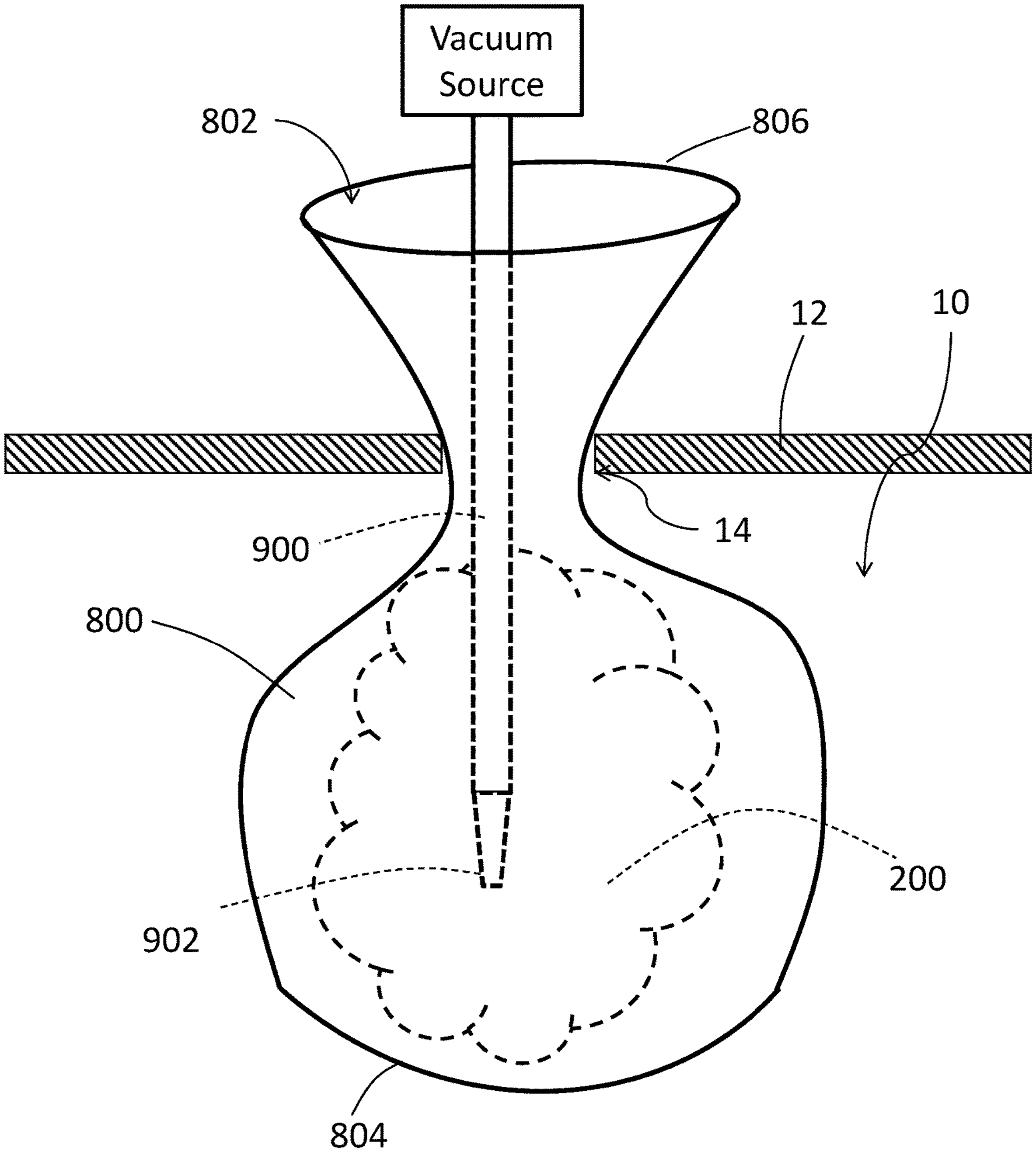
FIG. 20 shows a suction device inserted into the interior of the tissue specimen bag of FIG. 19 according to one embodiment of the present invention.
Figure 21:
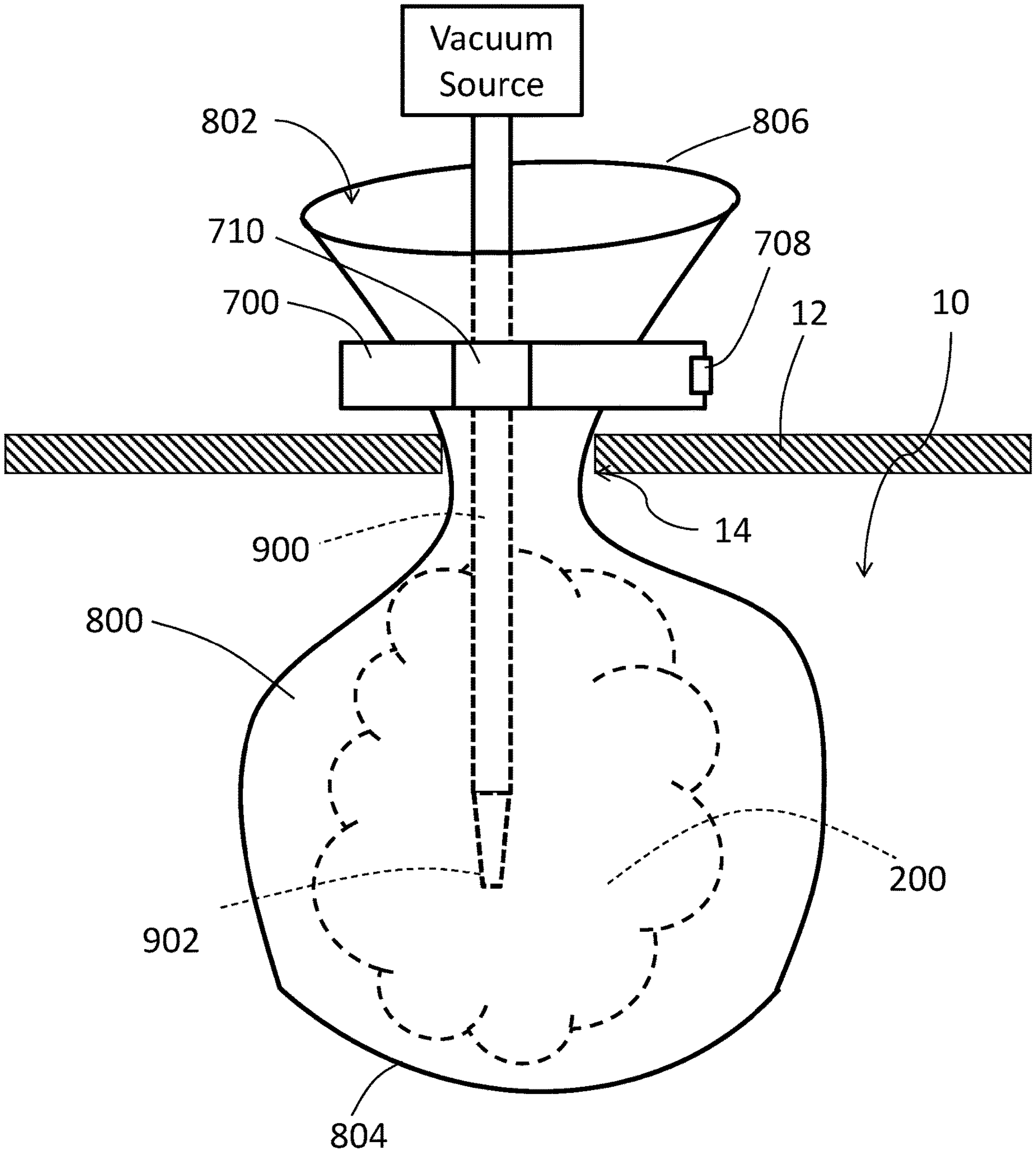
FIG. 21 shows the clip of FIG. 16A in a closed positioned around the tissue specimen bag and suction device of FIG. 20 according to one embodiment of the present invention.

As shown in FIG. 20, a suction device 900 may then be inserted at least partially into the interior of bag 800 through opening 802. As described above, suction device 900, in some embodiments, may be a suction catheter having a tip 902 and connected to a vacuum source which is configured to remove gas from the interior of bag 800. Care should be taken such that suction device 900 does not puncture or rupture the walls of bag 800. After suction device 900 has been positioned within bag 800, clip 700 may be positioned around a portion of bag 800 which extends out of cavity 10 to form a hermetic seal as described above with respect to FIGS. 17A-18B. In particular, bag 800 may be positioned between first and second legs 702, 704 of clip 700 while clip 700 is in the open configuration. First and second legs 702, 704 can then pivoted toward each other to the closed configuration and secured with closure 708, causing clip 700 to clamp against the walls of bag 800 to create a hermetic seal. In certain preferred embodiments, clip 700 can be transitioned from the open configuration to the closed configuration by hand without the need for any additional tools. Furthermore, clip 700 preferably can be used to seal bag 800 without any additional materials being wrapped or tied around bag 800 (e.g., sutures, string, tape, etc.). Moreover, clip 700 should be positioned such that suction device 900 is received in between first and second collar portions 710, 712 through opening 714 when clip 700 is in the closed configuration. A portion of bag 800 surrounding suction device 900 will be hermetically sealed against suction device 900 by clip 700 according to these embodiments. In other embodiments, clip 700 may be placed around bag 800 before suction device 900 is inserted into bag 800. In these embodiments, suction device 900 may then be inserted through open end 802 of bag 800 and through opening 714 of clip 700 while clip 700 is in the closed configuration around bag 800.

Figure 22:
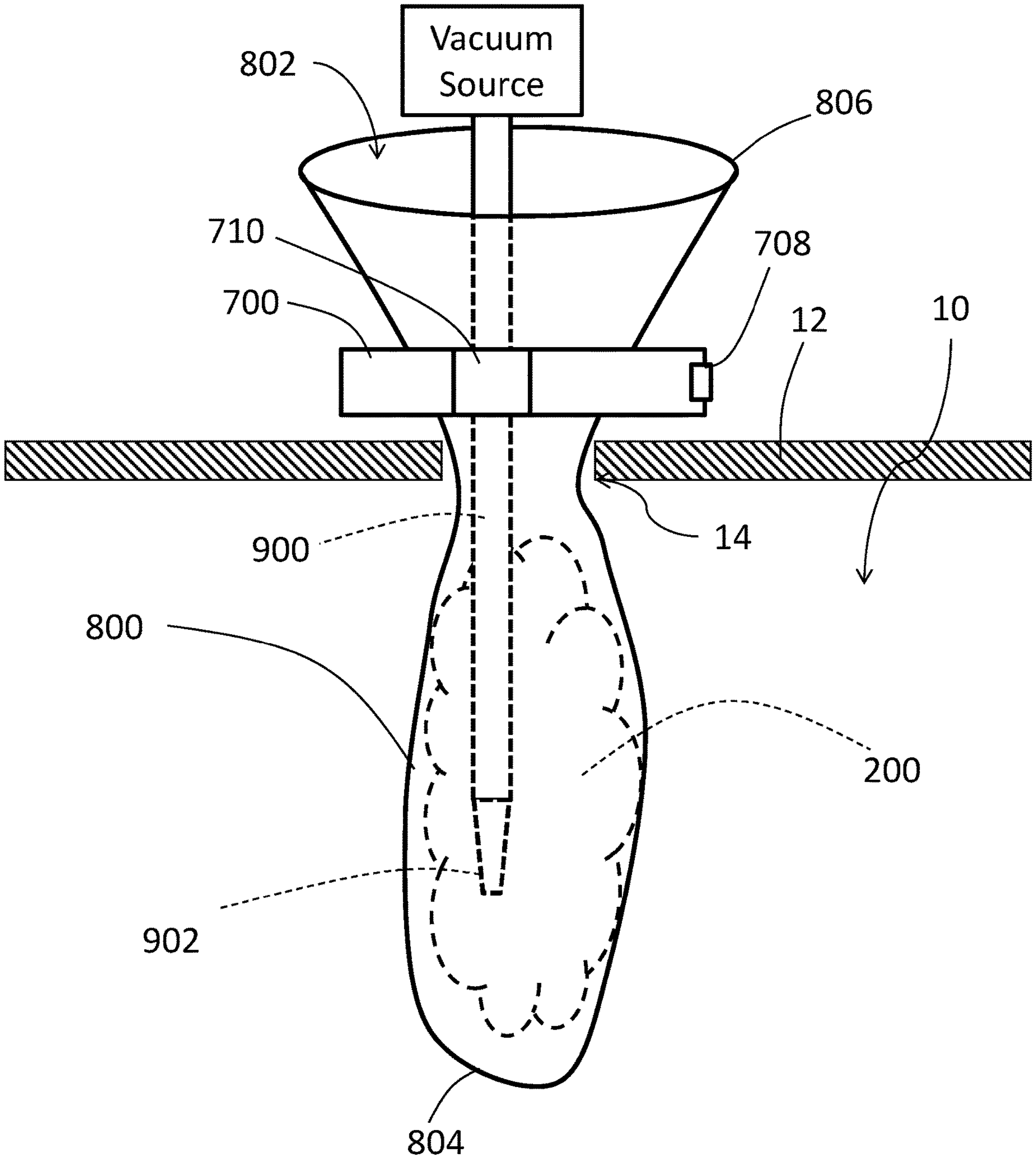
FIG. 22 shows the tissue specimen bag of FIG. 21 being deflated by the suction device according to one embodiment of the present invention.
Figure 23:
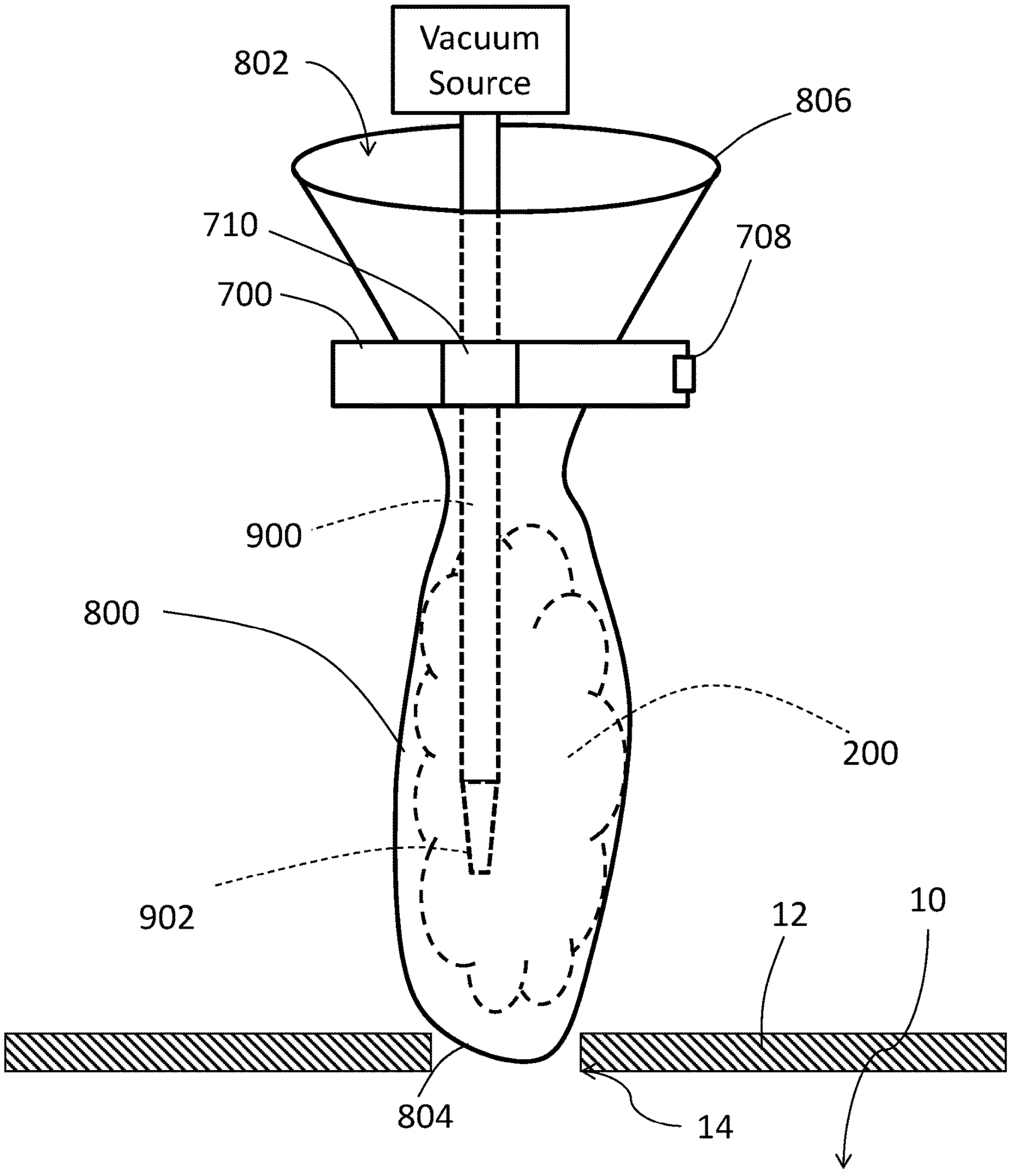
FIG. 23 shows the deflated tissue specimen bag of FIG. 22 withdrawn from the cavity according to one embodiment of the present invention.

Once clip 700 is properly positioned around bag 800 and suction device 900, the vacuum source can be activated to suction gas from the interior of bag 800 through suction device 900. In preferred embodiments, only gas is removed from the interior of bag 800 by suction device 900. Nevertheless, suction device 900 may further include a trap (not shown) connected between tip 902 and the vacuum source to capture non-gas materials (e.g., liquid) that may be suctioned by suction device 900. In some embodiments, removing gas from the interior of bag 800 causes compression of bag 800 and tissue specimen 200 contained therein, as illustrated in FIG. 22. For example, where tissue specimen 200 includes lung tissue, gas contained in the lung tissue can be evacuated during suctioning to cause collapse and compression of the lung tissue. In some embodiments, removing gas from the interior of bag 800 reduces the volume of tissue specimen 200 by at least 10%, by at least 20%, by at least 25%, by at least 30%, by at least 35%, by at least 40%, by at least 45%, by at least 50%, by at least 55%, by at least 60%, by at least 65%, by at least 70%, by at least 75%, or by at least 80%. Preferably, the volume of tissue specimen 200 is sufficiently reduced to allow for tissue specimen 200 within bag 800 to pass through incision 14 without having to enlarge incision 14 according to some embodiments. In some embodiments, however, where tissue specimen 200 cannot be sufficiently compressed by suctioning alone (e.g., where tissue specimen 200 contains very stiff or solid materials), some enlargement of incision 14 may be necessary before bag 800 can be completely withdrawn from cavity 10. FIG. 23 shows bag 800 containing tissue specimen 200 withdrawn from cavity 10 through incision 14 after sufficient suctioning. Bag 800 may be pulled by hand out of cavity 10 through incision 14, according to some embodiments. After removal of bag 800 from cavity 10, closure 708 may be disengaged to unclip clip 700 and allow removal of clip 700 from bag 800. Suction device 900 may then be withdrawn from the interior of bag 800, and tissue specimen 200 may then be removed from bag 800 for further examination or disposed of along with bag 800.

Figure 24:
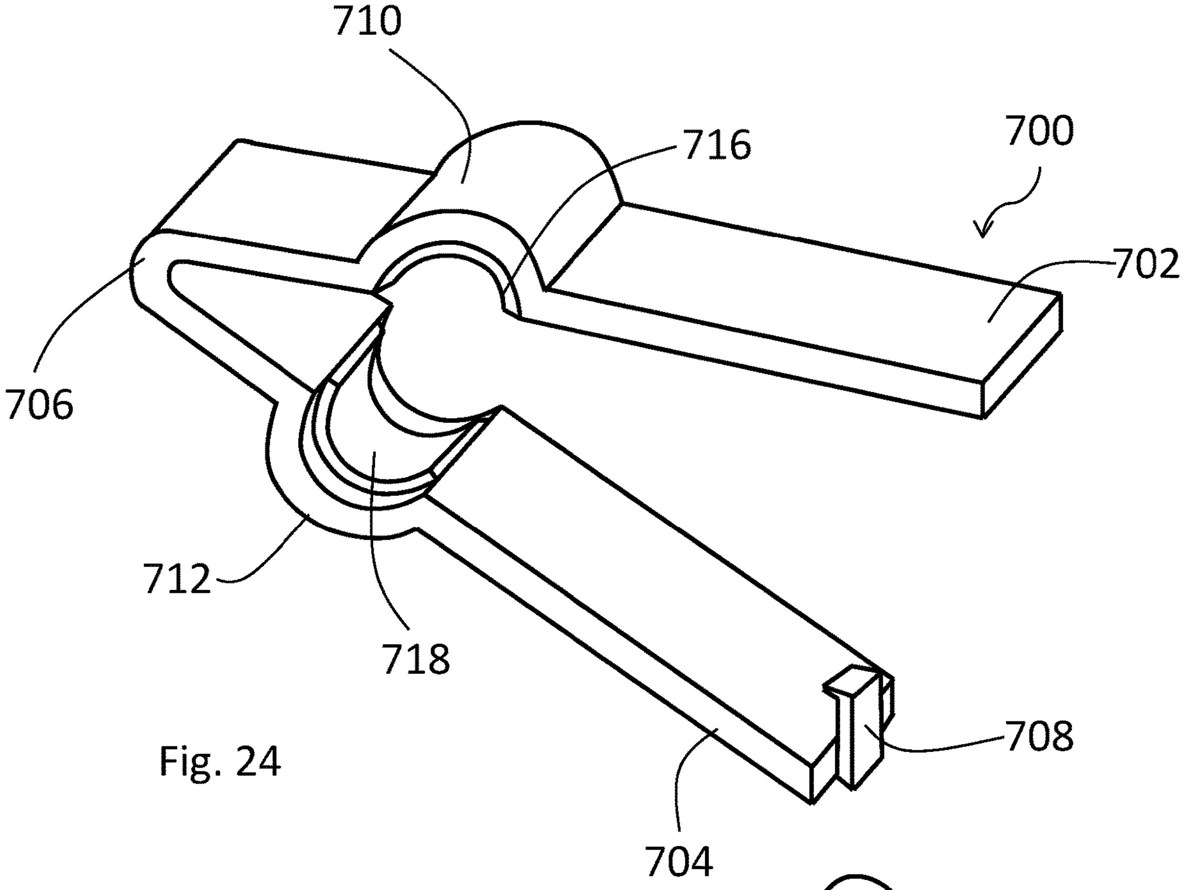
FIG. 24 shows the clip of FIG. 16A having an elastic layer according to one embodiment of the present invention.

FIG. 24 shows a variation of clip 700 according to a further embodiment of the present invention. In this embodiment, clip 700 includes at least one elastic layer 716, 718 provided on an internal surface of at least one of first leg 702 and second leg 704. In some embodiments, the at least one elastic layer 716, 718 may be positioned on an internal surface of first or second collar portions 710, 712. The elastic layer 716, 718 may be made from, for example, foam, rubber, silicone, elastomer, or other elastic material. In some embodiments, providing elastic layer 716, 718 may assist in forming a tighter seal against bag 800 and/or suction device 900. Moreover, in some embodiments, lining the first or second collar portions 710, 712 with the elastic layer 716, 718 may allow opening 714 to accommodate suction devices of different sizes.

Figure 25:
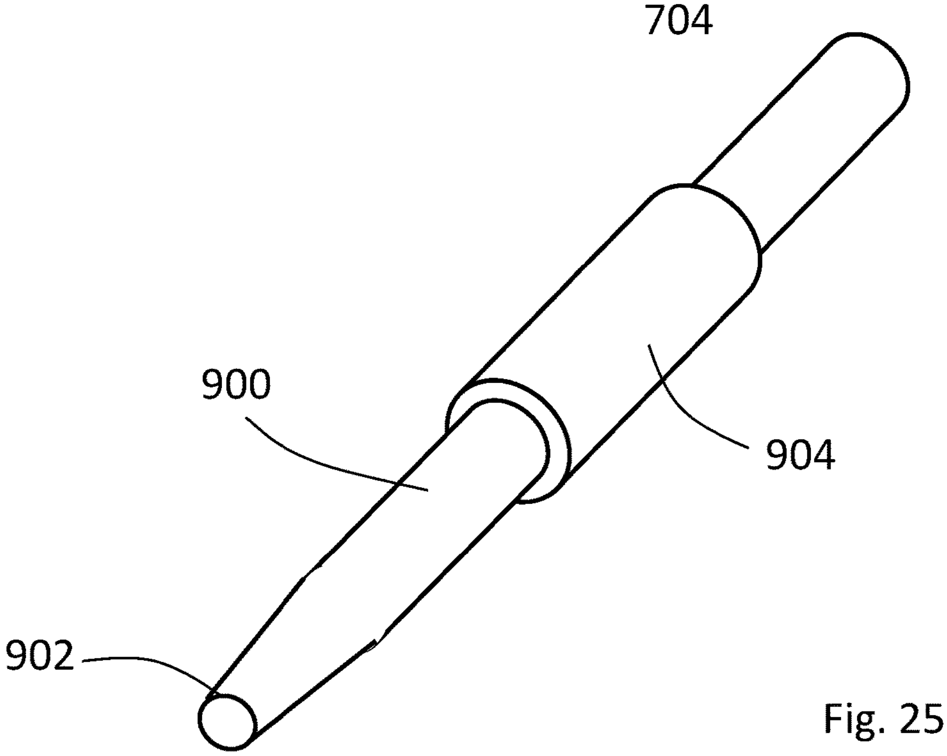
FIG. 25 shows the suction device of FIG. 17A provided with a cuff according to one embodiment of the present invention.

With reference to FIG. 25, suction device 900 may be provided with a cuff 904 that surrounds at least a portion suction device 900. In some embodiments, cuff 904 may be positioned around the portion of suction device 900 which is intended to be received within opening 714 of clip 700. In some embodiments, cuff 904 may be configured to create a tighter fit within opening 714 to improve the hermetic seal with bag 800. Cuff 904 may also be provided to increase the size (e.g., diameter) of suction device 900 if opening 714 is too large to create a sufficient seal around suction device 900. In use, according to some embodiments, the concavely curved internal surface of first and/or second legs 702, 704 which defines opening 714 may be positioned around the cuff 904 when clip 700 is positioned around bag 800 and suction device 900. Cuff 904, in some embodiments, may also be made from an elastic material, such as foam, rubber, silicone, etc.

Figure 26:
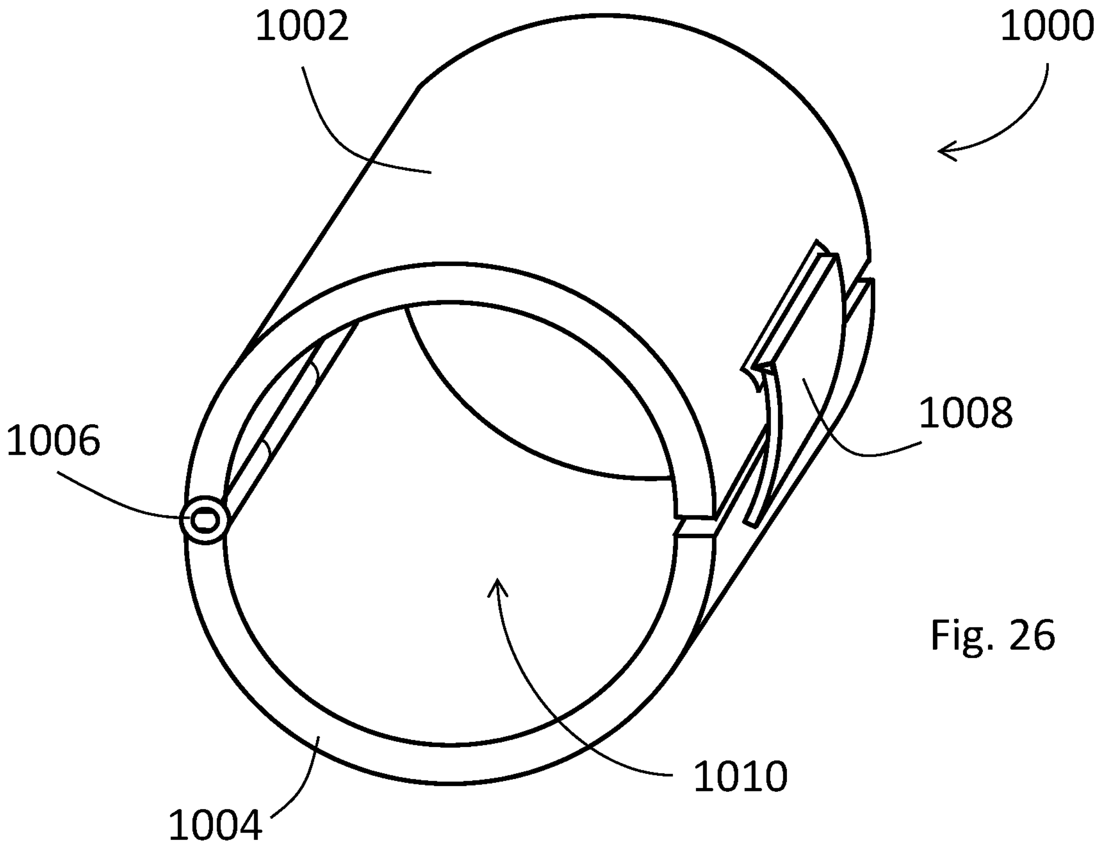
FIG. 26 shows a perspective view of a clip for a tissue specimen bag according to a further embodiment of the present invention in a closed configuration.
Figure 27:
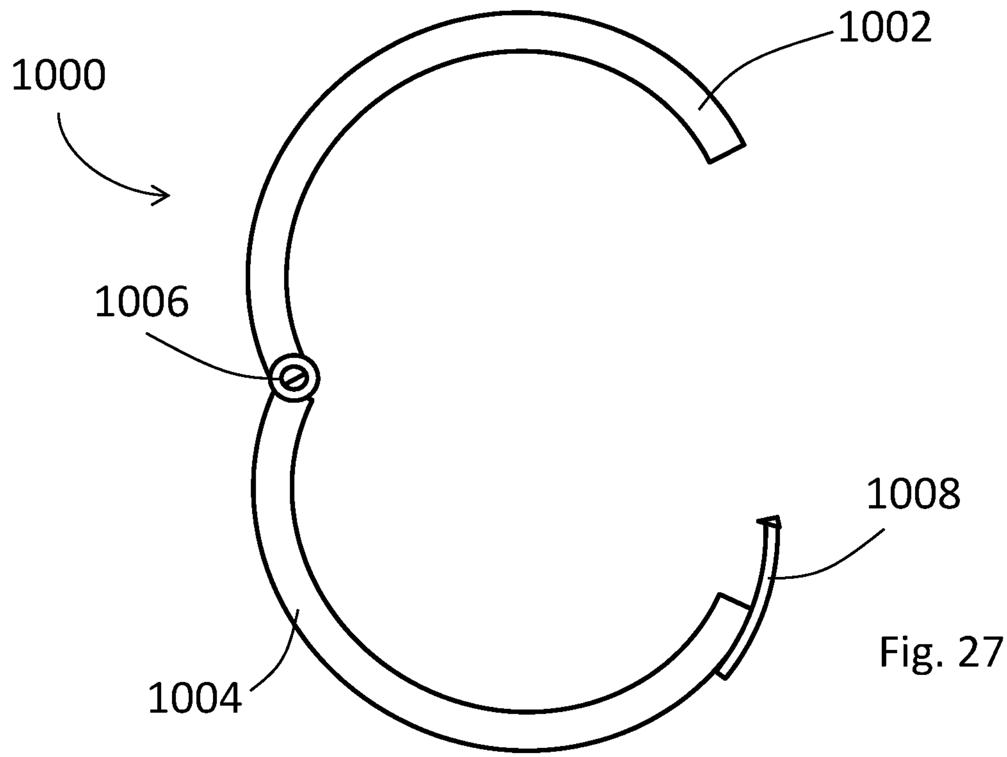
FIG. 27 shows an end view of the clip of FIG. 26 in an open configuration.

FIGS. 26 and 27 show a clip 1000 in accordance with yet another embodiment of the present invention. In some embodiments, clip 1000 includes a first leg 1002 and a second leg 1004 which are connected by a hinge 1006 and which are configured to move relative to each other between an open configuration (FIG. 27) and a closed configuration (FIG. 26) in a manner that may be similar to that described above with regards to clip 700. Hinge 1006 may be configured as any sort of hinge capable of allowing first and second legs 1002, 1004 to pivot towards or away from each other. In some embodiments, for example, hinge portion 1006 may include a pin about which first and second legs 1002, 1004 rotate. In other embodiments, hinge portion 1006 may be a living hinge wherein hinge portion 1006 is a flexible area between first and second legs 1002, 1004. In some embodiments, first and second legs 1002, 1004 are separate pieces which are connected by hinge portion 1006. In other embodiments, first and second legs 1002, 1004 and hinge portion 1006 are integrally formed from a single piece of material. First and second legs 1002, 1004 may be made from any suitable materials, for example, metals, plastics, polymers, composite materials, etc. In some embodiments, first and second legs 1002, 1004 are rigid or substantially rigid. In some embodiments, first and second legs 1002, 1004 may have a degree of flexibility. In certain embodiments, for example where clip 1000 is used for tissue specimen removal, clip 1000 is sterilized. In some embodiments, clip 1000 may be further provided with an anti-microbial substance or coating. Similar to the embodiment shown in FIG. 24, clip 1000 may further include at least one elastic layer provided on an internal surface of at least one of first leg 1002 and second leg 1004.

As with some embodiments of clip 700, clip 1000 may further include a closure 1008 which is configured to maintain first and second legs 1002, 1004 in the closed configuration. In some embodiments, closure 1008 may be configured as a latch, hook, snap fitting, or any other suitable mechanical feature capable of securing first leg 1002 relative to second leg 1004 in the closed configuration. In some embodiments, closure 1008 may include a protrusion which extends from one of first leg 1002 or second leg 1004 (as illustrated) and which is configured to contact and engage with the other leg in the closed configuration. In some embodiments, closure 1008 may include a first feature on first leg 1002 (e.g., hook) which engages with a second feature (e.g., loop) on second leg 1004 to secure first and second legs 1002, 1004 together. In some embodiments, closure 1008 includes features on first and second legs 1002, 1004 which are configured to interlock. In some embodiments, closure 1008 may be positioned at or proximate a free end of first leg 1002 and/or second leg 1004 which is opposite hinge portion 1006. In other embodiments, closure 1008 may include a device separable from clip 1000. For example, in some embodiments, closure 1008 may include a separate clamping device or fastener which may be applied to first and second legs 1002, 1004 in the closed configuration.

Unlike clip 700 as illustrated in FIGS. 16A-18B, substantially the entire length of first and second legs 1002, 1004 may be shaped to define an opening 1010 in the closed configuration which is sized and shaped to hermitically seal bag 800 around suction device 900. In some embodiments, at least one of first leg 1002 and second leg 1004 includes a concavely curved internal surface which at least partially defines opening 1010. For example, as shown in FIG. 26, substantially the entire length of first and second legs 1002, 1004 between hinge portion 1006 and closure 1008 may be curved such that clip 1000 is generally configured as a hollow cylinder in the closed configuration.

Figure 28:
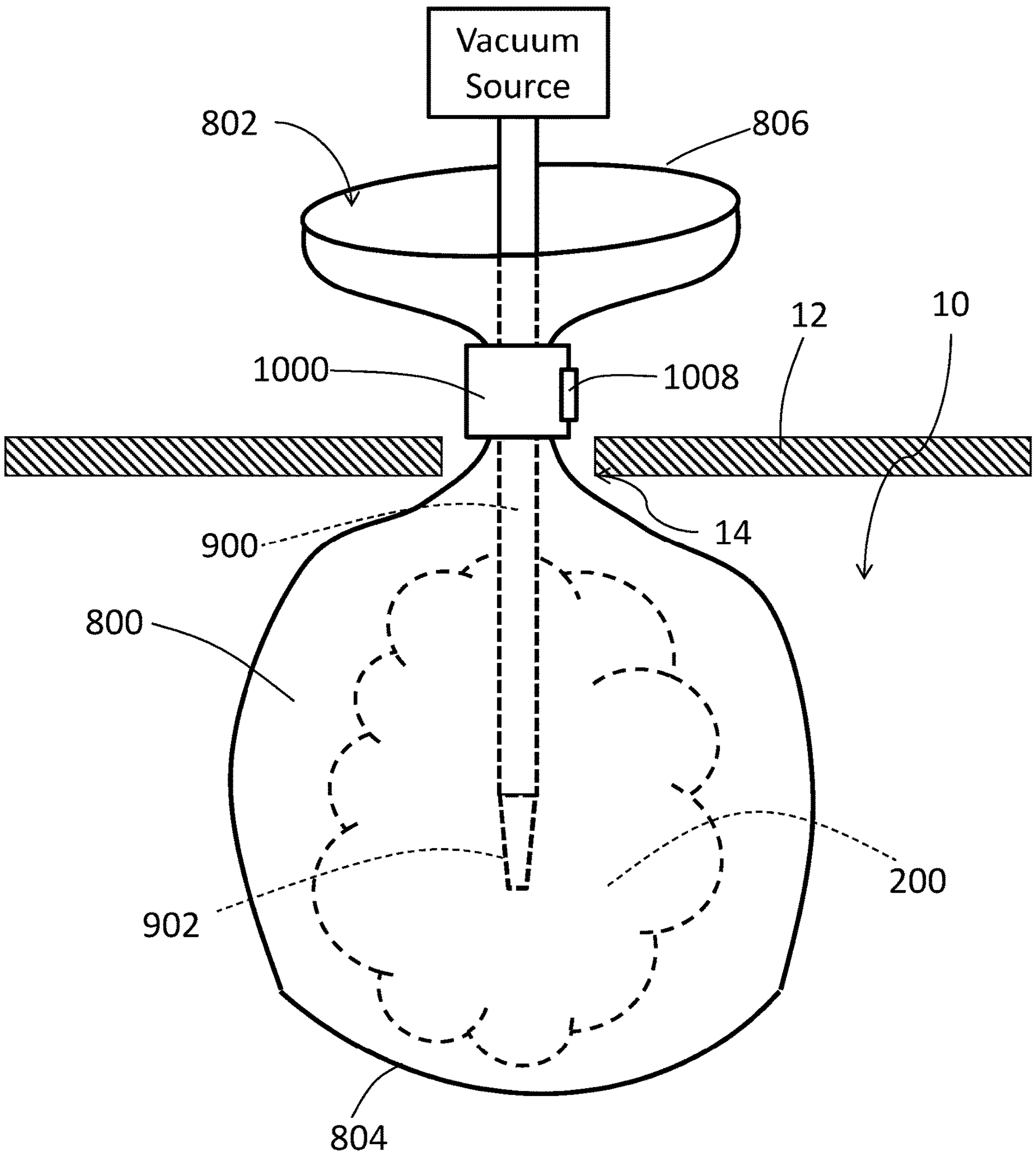
FIG. 28 shows the clip of FIG. 26 in a closed positioned around a tissue specimen bag and suction device inserted into the tissue specimen bag according to one embodiment of the present invention.

In some embodiments, clip 1000 may be used in a manner similar to clip 700 as described above in connection with FIGS. 19-23. For example, as shown in FIG. 28, clip 1000 may be positioned around a portion of bag 800 which extends out of cavity 10 to form a hermetic seal. In particular, bag 800 may be positioned between first and second legs 1002, 1004 of clip 1000 while clip 1000 is in the open configuration. First and second legs 1002, 1004 can then pivoted toward each other to the closed configuration and secured with closure 1008, causing clip 1000 to clamp around and/or against the walls of bag 800 to create a hermetic seal around suction device 900. Where suction device 900 includes a cuff 904 as described above, the concavely curved internal surface of first and/or second legs 1002, 1004 which defines opening 1010 may be positioned around the cuff 904 when clip 1000 is positioned around bag 800 and suction device 900. In certain preferred embodiments, clip 1000 can be transitioned from the open configuration to the closed configuration by hand without the need for any additional tools. Furthermore, clip 1000 preferably can be used to hermetically seal bag 800 around suction device 900 without any additional materials being wrapped or tied around bag 800 (e.g., sutures, string, tape, etc.). Once clip 1000 is properly positioned around bag 800 and suction device 900 such that a hermetic seal is formed, the vacuum source can be activated to suction gas from the interior of bag 800 through suction device 900.

Figure 29:
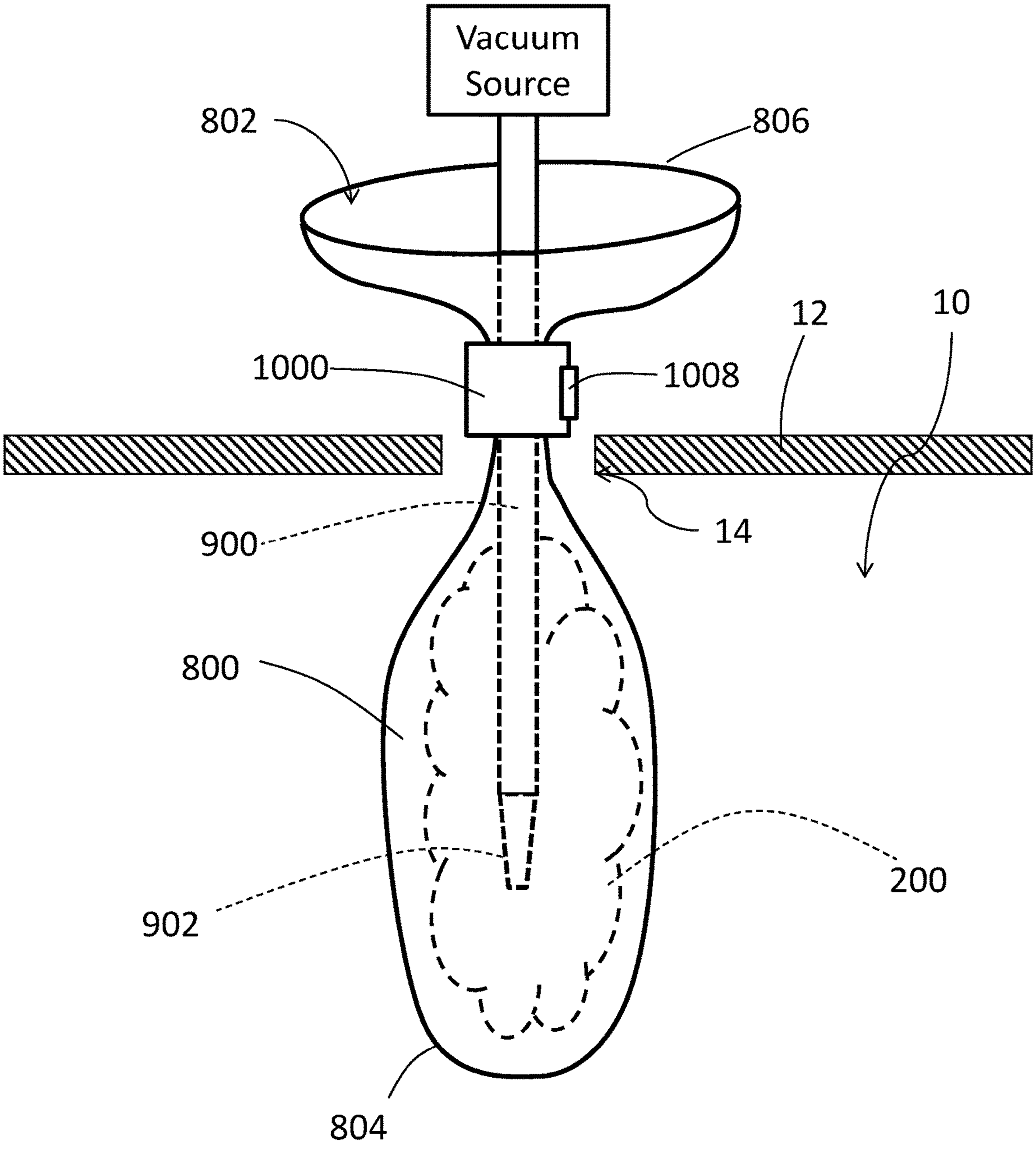
FIG. 29 shows the tissue specimen bag of FIG. 28 being deflated by the suction device according to one embodiment of the present invention.

In some embodiments, removing gas from the interior of bag 800 causes compression of bag 800 and tissue specimen 200 contained therein, as illustrated in FIG. 29. For example, where tissue specimen 200 includes lung tissue, gas contained in the lung tissue can be evacuated during suctioning to cause collapse and compression of the lung tissue. In some embodiments, removing gas from the interior of bag 800 reduces the volume of tissue specimen 200 by at least 10%, by at least 20%, by at least 25%, by at least 30%, by at least 35%, by at least 40%, by at least 45%, by at least 50%, by at least 55%, by at least 60%, by at least 65%, by at least 70%, by at least 75%, or by at least 80%. Preferably, the volume of tissue specimen 200 is sufficiently reduced to allow for tissue specimen 200 within bag 800 to pass through incision 14 without having to enlarge incision 14 according to some embodiments. In some embodiments, however, where tissue specimen 200 cannot be sufficiently compressed by suctioning alone (e.g., where tissue specimen 200 contains very stiff or solid materials), some enlargement of incision 14 may be necessary before bag 800 can be completely withdrawn from cavity 10.

Similar to the other embodiments described above, after bag 800 containing tissue specimen 200 may be withdrawn from cavity 10 through incision 14 after sufficient suctioning. Bag 800 may be pulled by hand out of cavity 10 through incision 14, according to some embodiments. After removal of bag 800 from cavity 10, closure 1008 may be disengaged to unclip clip 1000 and allow removal of clip 1000 from bag 800. Suction device 900 may then be withdrawn from the interior of bag 800, and tissue specimen 200 may then be removed from bag 800 for further examination or disposed of along with bag 800.

It should be understood that various changes, substitutions, and alterations can be made herein without departing from the spirit and scope of the invention as defined by the appended claims. It should also be apparent that individual elements identified herein as belonging to a particular embodiment may be included in other embodiments of the invention. Moreover, the scope of the present application is not intended to be limited to the exemplary embodiments of the processes, machines, manufactures, compositions of matter, means, methods and steps that are shown and described, but it is intended to cover modifications within the spirit and scope of the present invention as defined by the claims. As one of ordinary skill in the art will readily appreciate from the disclosure herein, processes, machines, manufactures, compositions of matter, means, methods, or steps that perform substantially the same function or achieve substantially the same result as the corresponding embodiments described herein may be utilized according to the present invention.

What is claimed is:

1. A device for tissue specimen removal comprising:
a sterilized bag comprising an open end;
a closed end opposite of the open end;
flexible walls extending between the open end and the closed end that define an interior space of the bag;
a spring element configured to open the open end of the bag; and
a clip comprising a first leg and a second leg, wherein:
at least one of the first leg and the second leg includes a concavely curved internal surface;
the clip is positioned around the bag and a catheter attached to a vacuum source;
the concavely curved internal surface is configured to be positioned around a portion of the catheter; and
moving the first leg and the second leg of the clip seals the bag around the catheter.

2. The device of claim 1, wherein the first leg and the second leg are connected by a hinge portion configured to allow the first leg and the second leg to pivot toward each other.

3. The device of claim 1, wherein the clip further comprises a closure for securing the first leg and the second leg together in a closed configuration.

4. The device of claim 1, wherein the bag is sterilized with radiation, heat, steam, chemical treatments, or a combination thereof.

5. The device of claim 1, wherein the bag comprises an anti-microbial substance or coating.

6. The device of claim 1, wherein the spring element comprises a loop or portion thereof made from an elastic material and extends at least partially around the open end of the bag.

7. The device of claim 1, wherein the spring element extends around the entire open end of the bag.

* * * * *